US006562598B1

(12) United States Patent
Himmelspach et al.

(10) Patent No.: US 6,562,598 B1
(45) Date of Patent: May 13, 2003

(54) FACTOR X DELETION MUTANTS AND ANALOGUES THEREOF

(75) Inventors: Michele Himmelspach, Leopoldsdorf (AT); Michael Pfleiderer, Darmstadt (DE); Falko-Guenter Falkner, Orth/Donau (AT); Johann Eibl, Vienna (AT); Friedrich Dorner, Vienna (AT); Uwe Schlokat, Orth/Donau (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/367,777

(22) PCT Filed: Feb. 27, 1998

(86) PCT No.: PCT/AT98/00046

§ 371 (c)(1),
(2), (4) Date: Nov. 18, 1999

(87) PCT Pub. No.: WO98/38318

PCT Pub. Date: Sep. 3, 1998

(30) Foreign Application Priority Data

Feb. 27, 1997 (AU) ................................... 336/97

(51) Int. Cl.[7] ................. C12P 21/06; C07K 114/00

(52) U.S. Cl. ................. 435/69.6; 514/2; 530/380

(58) Field of Search ................. 514/12, 2, 8, 21; 424/94.64; 530/384, 395; 435/69.1, 69.2, 69.6

(56) References Cited

U.S. PATENT DOCUMENTS

| | | | |
|---|---|---|---|
| 4,501,731 A | 2/1985 | Tishkoff et al. | |
| 5,460,950 A | 10/1995 | Barr et al. | |
| 5,597,799 A | * 1/1997 | Wolf | 514/12 |
| 5,635,481 A | * 6/1997 | Wolf | 514/12 |

FOREIGN PATENT DOCUMENTS

| | | |
|---|---|---|
| AT | 366 916 | 4/1980 |
| EP | 382 783 B | 6/1985 |
| EP | 0 651 054 A1 | 2/1994 |
| EP | 0 714 987 A2 | 9/1995 |
| EP | 0 775 750 A2 | 11/1996 |

OTHER PUBLICATIONS

Wells et al. Additivity of Mutational Effects in Proteins. Biochemistry (1990) vol. 29, No. 37, pp. 8509–8517.*
Ngo et al. Computational Complexity, Protein Structure Prediction and the Levinthal Paradox in The Protein Folding Problem and Tertiary Strucure, 1994, K. Merz, Jr. and Le Grand, Ed., Birkhauser, Boston.*
Wolf D.L. et al., "Design of Constructs for the Expression of Biologically Active Recombinant Human Factors X and Xa. Kinetic Analysis of the Expressed Proteins", *J. Biol. Chem.*, vol. 21, 1991, pp. 13726–13730, XP002065182.
Leytus S. et al., "Gene for Human Factor X: A Blood Coagulation Factor Whose Gene Organization is Essentially Identical With That of Factor IX and Protein C", *Biochem.*, vol. 25, 1986, pp. 5098–5102, XP002065183.
International Search Report for PCT/AT98/00046, dated Jun. 4, 1998.
Bajaj, S.P. et al., "Simultaneous Purification of Bovine Prothrombin and Factor X", *J. Biol Chem.*, vol. 248, 1973, pp. 7729–7741.
Clackson, T. et al., "PCR A Practical Approach; General Applications of PCR to Gene Cloning and Manipulation", Eds. McPherson, Quirke and Taylor, 1991, pp. 187–214.
Eby, C.S. et al., "Characterization of the Structure and Function of the Carboxy Terminal Peptide of Human Factor X", *Blood*, vol. 80, Supp. 1, 1214, 1992, p. 1215.
Elsinger, F., "Laboratory Tests of Activated Prothrombin Complex Preparations;Activated Prothrombin Complex Concentrates", Eds. Mariani, Russo and Mandelli, 1982, pp. 77–87.
Fair, D.S. and Bahnak, B.R., "Human Hepatoma Cells Secrete Single Chain Factor X, Prothrombin, and Antithrombin III", *Blood*, vol. 64, 1984, pp. 194–204.
Fung, M.R. et al., "Characterization of an Almost Full–Length cDNA Coding for Human Blood Coagulation Factor X", *PNAS*, vol. 82, 1985, pp. 3591–3595.
Giles, A.R. et al., "A Combination of Factor Xa and Phosphatidylcholine–phosphatidylserine Vesciles Bypasses Factor VIII in vivo", *British J. of Haematology*, vol. 69, 1988, pp. 491–497.
Gordon, V.M. et al., "Proteolytic Activation of Bacterial Toxins by Eukaryotic Cells Is Performed by Furin and by Additional Cellular Proteases", *Infect. Immunol.* vol. 63, 1995, pp. 82–87.
Jesty, J. et al., "The Mechanism of Activation of Factor X: Kinetic Control of Alternative Pathways Leading to the Formation of Activated Factor X", *J. Biol. Chem.*, vol. 249, 1974, pp. 5614–5622.
Mertens, K. and Bertine, R.M., "Pathways in the Activation of Human Coagulation Factor X", *Biochem. J.*, vol. 185, 1980, pp. 647–658.

(List continued on next page.)

*Primary Examiner*—Karen Cochrane Carlson
*Assistant Examiner*—Sheridan Snedden
(74) *Attorney, Agent, or Firm*—Townsend and Townsend and Crew LLP

(57) ABSTRACT

Factor XΔ analogues are provided, as well as pharmaceutical preparations containing such analogues and methods of preparing such analogues. The factor XΔ analogues have a deletion of the amino acids Arg180 to Arg234 and a modification in the region of the amino acid sequence between Gly173 and Arg179 of the factor X amino acid sequence. Such analogues can include a processing site not normally present in factor X, thus allowing for selective conversion of the analogue to an active form. The analogues and preparations have utility in the treatment of a number of blood coagulation disorders.

56 Claims, 12 Drawing Sheets

OTHER PUBLICATIONS

Messier, T.L. et al., "Cloning and Expression in COS–1 Cells of a Full–Length cDNA Encoding Human Coagulation Factor X", *Gene*, vol. 90, 1991, pp. 291–294.

Moehring, J.M. and Moehring, T.J., "Strains of CHO–K1 Cells Resistant to Pseudomonas Exotoxin A and Cross–Resistant to Diphtheria Toxin and Viruses", *Infection and Immunity*, vol. 41, 1983, pp. 998–1009.

Ohnishi, Y. et al., "A Furin–Defective Cell Line Is Able to Process Correctly the gp160 of Human Immunodeficienty Virus Type 1", *J. Virol.*, vol. 68, 1994, pp. 4075–4079.

Pryzdial, E.L.G. and Kessler, G.E., "Autoproteolysis or Plasmin–mediated Cleavage of Factor Xaα Exposes a Plasminogen Binding Site and Inhibits Coagulation", *J. Biol. Chem.*, vol. 271, 1996, pp. 16614–16620.

Pryzdial, E.L.G. and Kessler, G.E., "Kinetics of Blood Coagulation Factor Xaα Autoproteolytic Conversion to Factor Xaβ", *J. Biol. Chem.*, vol. 271, 1996, pp. 16621–16626.

Rehemtulla, A. and Kaufman, R.J., "Preferred Sequence Requirements for Cleavage of Pro–von Willebrand Factor by Propeptide–Processing Enzymes", *Blood*, vol. 79, 1992, pp. 2349–2355.

Rudolph, A.E. et al., "Expression, Purification, and Characterization of Recombinant Human Factor $X^1$", *Protein Expression& Purification*, vol. 10, pp. 373–378.

Teng, C. and Seegers, W.H., "Production of Factor X and Factor Xa Variants With Thrombin, Acutin and by Autolysis", *Thrombosis Res.* vol. 22, 1981, pp. 213–220.

Urlaub, G. and Chasin, L.A., "Isolation of Chinese Hamster Cell Mutants Deficient in Dihydrofolate Reductase Activity", *PNAS*, vol. 77, 1980, pp. 4216–4220.

Wallin, R. et al., "Intracellular Proteolytic Processing of the Two–Chain Vitamin K–Dependent Coagulation Factor X", *Thrombosis Res.* vol. 73, 1994, pp. 395–403.

Watzke, H.H. and High, Katherine A., "Factor X", *Molecular Basis of Thrombosis and Hemostasis*, Eds. High & Roberts, 1995, pp. 239–255.

\* cited by examiner

```
                    (-40)
                      1
              Met Gly Arg Pro Leu His Leu Val Leu Leu Ser Ala Ser Leu Ala Gly Leu Leu Leu
              ATG GGG CGC CCA CTG CAC CTC GTC CTG CTC AGT GCC TCC CTG GCT GGC CTC CTG CTG
                           9           18          27          36          45          54

(-4)        (-1)
                                                                                40
Leu Gly Glu Ser Leu Phe Ile Arg Arg Glu Gln Ala Asn Asn Ile Leu Ala Arg Val Thr Arg
CTC GGG GAA AGT CTG TTC ATC CGC AGG GAG CAG GCC AAC AAC ATC CTG GCG AGG GTC ACG AGG
            66          75          84          93         102         111         120

(+1)
 41
Ala Asn Ser Phe Leu Glu Glu Met Lys Lys Gly His Leu Glu Arg Glu Cys Met Glu Glu Thr
GCC AAT TCC TTT CTT GAA GAG ATG AAG AAA GGA CAC CTC GAA AGA GAG TGC ATG GAA GAG ACC
           129         138         147         156         165         174         183

Cys Ser Tyr Glu Glu Ala Arg Glu Val Phe Glu Asp Ser Asp Lys Thr Asn Glu Phe Trp Asn
TGC TCA TAC GAA GAG GCC CGC GAG GTC TTT GAG GAC AGC GAC AAG ACG AAT GAA TTC TGG AAT
           192         201         210         219         228         237         246

Lys Tyr Lys Asp Gly Asp Gln Cys Glu Thr Ser Pro Cys Gln Asn Gln Gly Lys Cys Lys Asp
AAA TAC AAA GAT GGC GAC CAG TGT GAG ACC AGT CCT TGC CAG AAC CAG GGC AAA TGT AAA GAC
           255         264         273         282         291         300         309

Gly Leu Gly Glu Tyr Thr Cys Thr Cys Leu Glu Gly Phe Glu Gly Lys Asn Cys Glu Leu Phe
GGC CTC GGG GAA TAC ACC TGC ACC TGT TTA GAA GGA TTC GAA GGC AAA AAC TGT GAA TTA TTC
           318         327         336         345         354         363         372

Thr Arg Lys Leu Cys Ser Leu Asp Asn Gly Asp Cys Asp Gln Phe Cys His Glu Glu Gln Asn
ACA CGG AAG CTC TGC AGC CTG GAC AAC GGG GAC TGT GAC CAG TTC TGC CAC GAG GAA CAG AAC
           381         390         399         408         417         426         435

Ser Val Val Cys Ser Cys Ala Arg Gly Tyr Thr Leu Ala Asp Asn Gly Lys Ala Cys Ile Pro
TCT GTG GTG TGC TCC TGC GCC CGC GGG TAC ACC CTG GCT GAC AAC GGC AAG GCC TGC ATT CCC
           444         453         462         471         480         489         498

R6  R5  R4  R3  R2
                                 173 174 175 176 177 178 179 180 181 182 183
Thr Gly Pro Tyr Pro Cys Gly Lys Gln Thr Leu Glu Arg Arg Lys Arg Ser Val Ala Gln Ala
ACA GGG CCC TAC CCC TGT GGG AAA CAG ACC CTG GAA CGC AGG AAG AGG TCA GTG GCC CAG GCC
           507         516         525         534         543         552         561

Thr Ser Ser Ser Gly Glu Ala Pro Asp Ser Ile Thr Trp Lys Pro Tyr Asp Ala Ala Asp Leu
ACC AGC AGC AGC GGG GAG GCC CCT GAC AGC ATC ACA TGG AAG CCA TAT GAT GCA GCC GAC CTG
           570         579         588         597         606         615         624

Asp Pro Thr Glu Asn Pro Phe Asp Leu Leu Asp Phe Asn Gln Thr Gln Pro Glu Arg Gly Asp
GAC CCC ACC GAG AAC CCC TTC GAC CTG CTT GAC TTC AAC CAG ACG CAG CCT GAG AGG GGC GAC
           633         642         651         660         669         678         687
```

Fig.1A

```
                              R1
                     234 235
Asn Asn Leu Thr Arg Ile Val Gly Gly Gln Glu Cys Lys Asp Gly Glu Cys Pro Trp Gln Ala
AAC AAC CTC ACC AGG ATC GTG GGA GGC CAG GAA TGC AAG GAC GGG GAG TGT CCC TGG CAG GCC
        696         705         714         723         732         741         750

Leu Leu Ile Asn Glu Glu Asn Glu Gly Phe Cys Gly Gly Thr Ile Leu Ser Glu Phe Tyr Ile
CTG CTC ATC AAT GAG GAA AAC GAG GGT TTC TGT GGT GGA ACT ATT CTG AGC GAG TTC TAC ATC
        759         768         777         786         795         804         813

Leu Thr Ala Ala His Cys Leu Tyr Gln Ala Lys Arg Phe Lys Val Arg Val Gly Asp Arg Asn
CTA ACG GCA GCC CAC TGT CTC TAC CAA GCC AAG AGA TTC AAG GTG AGG GTA GGG GAC CGG AAC
        822         831         840         849         858         867         876

Thr Glu Gln Glu Glu Gly Gly Glu Ala Val His Glu Val Glu Val Val Ile Lys His Asn Arg
ACG GAG CAG GAG GAG GGC GGT GAG GCG GTG CAC GAG GTG GAG GTG GTC ATC AAG CAC AAC CGG
        885         894         903         912         921         930         939

Phe Thr Lys Glu Thr Tyr Asp Phe Asp Ile Ala Val Leu Arg Leu Lys Thr Pro Ile Thr Phe
TTC ACA AAG GAG ACC TAT GAC TTC GAC ATC GCC GTG CTC CGG CTC AAG ACC CCC ATC ACC TTC
        948         957         966         975         984         993         1002

Arg Met Asn Val Ala Pro Ala Cys Leu Pro Glu Arg Asp Trp Ala Glu Ser Thr Leu Met Thr
CGC ATG AAC GTG GCG CCT GCC TGC CTC CCC GAG CGT GAC TGG GCC GAG TCC ACG CTG ATG ACG
        1011        1020        1029        1038        1047        1056        1065

Gln Lys Thr Gly Ile Val Ser Gly Phe Gly Arg Thr His Glu Lys Gly Arg Gln Ser Thr Arg
CAG AAG ACG GGG ATT GTG AGC GGC TTC GGG CGC ACC CAC GAG AAG GGC CGG CAG TCC ACC AGG
        1074        1083        1092        1101        1110        1119        1128

Leu Lys Met Leu Glu Val Pro Tyr Val Asp Arg Asn Ser Cys Lys Leu Ser Ser Ser Phe Ile
CTC AAG ATG CTG GAG GTG CCC TAC GTG GAC CGC AAC AGC TGC AAG CTG TCC AGC AGC TTC ATC
        1137        1146        1155        1164        1173        1182        1191

Ile Thr Gln Asn Met Phe Cys Ala Gly Tyr Asp Thr Lys Gln Glu Asp Ala Cys Gln Gly Asp
ATC ACC CAG AAC ATG TTC TGT GCC GGC TAC GAC ACC AAG CAG GAG GAT GCC TGC CAG GGG GAC
        1200        1209        1218        1227        1236        1245        1254

Ser Gly Gly Pro His Val Thr Arg Phe Lys Asp Thr Tyr Phe Val Thr Gly Ile Val Ser Trp
AGC GGG GGC CCG CAC GTC ACC CGC TTC AAG GAC ACC TAC TTC GTG ACA GGC ATC GTC AGC TGG
        1263        1272        1281        1290        1399        1308        1317

Gly Glu Ser Cys Ala Arg Lys Gly Lys Tyr Gly Ile Tyr Thr Lys Val Thr Ala Phe Leu Lys
GGA GAG AGC TGT GCC CGT AAG GGG AAG TAC GGG ATC TAC ACC AAG GTC ACC GCC TTC CTC AAG
        1326        1335        1344        1353        1362        1371        1380

469 470                 475 476              480
Trp Ile Asp Arg Ser Met Lys Thr Arg Gly Leu Pro Lys Ala Lys Ser His Ala Pro Glu Val
TGG ATC GAC AGG TCC ATG AAA ACC AGG GGC TTG CCC AAG GCC AAG AGC CAT GCC CCG GAG GTC
        1389        1398        1407        1416        1425        1434        1443

488
Ile Thr Ser Ser Pro Leu Lys TER
ATA ACG TCC TCT CCA TTA AAG TGA
        1452        1461    1467

PRE-/PROPEPTIDE
"CONNECTING" TRIPEPTIDE       Fig.1B
ACTIVATION PEPTIDE
``` t= period of incubation at 37°C (hours)

SEQUENCE LISTING (1) GENERAL INFORMATION:

(iii) NUMBER OF SEQUENCES: 145

(2) INFORMATION FOR SEQ ID NO: 1:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 1:

ATTACTCGAG AAGCTTACCA TGGGGCGCCC ACTG    34

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

ATTACAATTG CTGCAGGGAT CCAC                                                          24

(2) INFORMATION FOR SEQ ID NO: 3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GGCCCTACCC CTGTGGGAAA CAGGACTTCA CCAGGGTG                                  38

(2) INFORMATION FOR SEQ ID NO: 4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

CACCCTGGTG AAGTCCTGTT TCCCACAGGG GTAG                                          34

(2) INFORMATION FOR SEQ ID NO: 5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GGCCCTACCC CTGTGGGAAA CAGACCCTGG AACGGACC                                  38

(2) INFORMATION FOR SEQ ID NO: 6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

GGTCCGTTCC AGGGTCTGTT TCCCACAGGG GTAG                                          34

(2) INFORMATION FOR SEQ ID NO: 7:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 7:

GGCCCTACCC CTGTGGGAAA CAGATCAAGC CCAGGATC                        38

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

CTGGGCTTGA TCTGTTTCCC ACAGGGGTAG                                 30

(2) INFORMATION FOR SEQ ID NO: 9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

GGCCCTACCC CTGTGGGAAA CAGAGCATGA CCAGGATC                        38

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

CTGGTCATGC TCTGTTTCCC ACAGGGGTAG                                 30

(2) INFORMATION FOR SEQ ID NO: 11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GGCCCTACCC CTGTGGGAAA CAGATGAAAA CGAGGATC                        38

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 12:

CTCGTTTTCA TCTGTTTCCC ACAGGGGTAG                30

(2) INFORMATION FOR SEQ ID NO: 13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GGCCCTACCC CTGTGGGAAA CAGATCGAGG GAAGGATC        38

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

CTTCCCTCGA TCTGTTTCCC ACAGGGGTAG                30

(2) INFORMATION FOR SEQ ID NO: 15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GGCCCTACCC CTGTGGGAAA CAGAGGAGGA AGAGGATC        38

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

CTCTTCCTCC TCTGTTTCCC ACAGGGGTAG                30

(2) INFORMATION FOR SEQ ID NO: 17:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

GGCCCTACCC CTGTGGGAAA CAGAGGGTGA GGAGGATC                          38

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

CTCCTCACCC TCTGTTTCCC ACAGGGGTAG                                   30

(2) INFORMATION FOR SEQ ID NO: 19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GGCCCTACCC CTGTGGGAAA CAGAGGAGGA GGAGGATC                          38

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

CTCCTCCTCC TCTGTTTCCC ACAGGGGTAG                                   30

(2) INFORMATION FOR SEQ ID NO: 21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

GGCCCTACCC CTGTGGGAAA CAGAGGCCCA AGAGGATC                          38

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

CTCTTGGGCC TCTGTTTCCC ACAGGGGTAG                                   30

(2) INFORMATION FOR SEQ ID NO: 23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

GGCCCTACCC CTGTGGGAAA CAGATCAGGA AGAGGATC                      38

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CTCTTCCTGA TCTGTTTCCC ACAGGGGTAG                               30

(2) INFORMATION FOR SEQ ID NO: 25:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

GGCCCTACCC CTGTGGGAAA CAGAGGAGCA AGAGGATC                      38

(2) INFORMATION FOR SEQ ID NO: 26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

CTCTTGCTCC TCTGTTTCCC ACAGGGGTAG                               30

(2) INFORMATION FOR SEQ ID NO: 27:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

GGCCCTACCC CTGTGGGAAA CAGAGGGTCA CGAGGATC                      38

(2) INFORMATION FOR SEQ ID NO: 28:

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

CTCGTGACCC TCTGTTTCCC ACAGGGGTAG                                         30

(2) INFORMATION FOR SEQ ID NO: 29:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

GGCCCTACCC CTGTGGGAAA CAGAGGCTGA AAAGGATC                                 38

(2) INFORMATION FOR SEQ ID NO: 30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

CTTTTCAGCC TCTGTTTCCC ACAGGGGTAG                                         30

(2) INFORMATION FOR SEQ ID NO: 31:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

GGCCCTACCC CTGTGGGAAA CAGCCCCAAG GAAGGATC                                 38

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

CTTCCTTGGG GCTGTTTCCC ACAGGGGTAG                                         30

(2) INFORMATION FOR SEQ ID NO: 33:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

GGCCCTACCC CTGTGGGAAA CAGACGAGCA CGAGGATC                           38

(2) INFORMATION FOR SEQ ID NO: 34:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 34:

CTCGTGCTCG TCTGTTTCCC ACAGGGGTAG                                    30

(2) INFORMATION FOR SEQ ID NO: 35:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 35:

GGCCCTACCC CTGTGGGAAA CAGACCCTGG AACGGATC                           38

(2) INFORMATION FOR SEQ ID NO: 36:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 36:

CGTTCCAGGG TCTGTTTCCC ACAGGGGTAG                                    30

(2) INFORMATION FOR SEQ ID NO: 37:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 37:

GTCACCGCCT TCCTCAAGTG GATCGACAGG TCCATGAAAA CCAGGTGAA               49

(2) INFORMATION FOR SEQ ID NO: 38:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 38:

CTAGTTCACC TGGTTTTCAT GGACCTGTCG ATCCACTTGA GGAAGGCG            48

(2) INFORMATION FOR SEQ ID NO: 39:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

GTCACCGCCT TCCTCAAGTG GATCGACAGG TCCATGAAAA CCAAGGGCTT GCCCAAG            57

(2) INFORMATION FOR SEQ ID NO: 40:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

TTGGCCTTGG GCAAGCCCTT GGTTTTCATG GACCTGTCGA TCCACTTGAG GAAGGCG            57

(2) INFORMATION FOR SEQ ID NO: 41:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 41:

GCCAAGAGCC ATGCCCCGGA GGTCATAACG TCCTCTCCAT TAAAGTGAGA TCCCA            55

(2) INFORMATION FOR SEQ ID NO: 42:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 42:

CTAGTGGGAT CTCACTTTAA TGGAGAGGAC GTTATGACCT CCGGGGCATG GCTC            54

(2) INFORMATION FOR SEQ ID NO: 43:

(i) SEQUENCE CHARACTERISTICS:
        (A) LENGTH: 1467 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1...1467
        (D) OTHER INFORMATION: Factor X (xi) SEQUENCE DESCRIPTION: SEQ ID NO: 43:

```
ATG GGG CGC CCA CTG CAC CTC GTC CTG CTC AGT GCC TCC CTG GCT GGC        48
Met Gly Arg Pro Leu His Leu Val Leu Leu Ser Ala Ser Leu Ala Gly
 1               5                  10                  15

CTC CTG CTG CTC GGG GAA AGT CTG TTC ATC CGC AGG GAG CAG GCC AAC        96
Leu Leu Leu Leu Gly Glu Ser Leu Phe Ile Arg Arg Glu Gln Ala Asn
            20                  25                  30

AAC ATC CTG GCG AGG GTC ACG AGG GCC AAT TCC TTT CTT GAA GAG ATG       144
Asn Ile Leu Ala Arg Val Thr Arg Ala Asn Ser Phe Leu Glu Glu Met
                35                  40                  45

AAG AAA GGA CAC CTC GAA AGA GAG TGC ATG GAA GAG ACC TGC TCA TAC       192
Lys Lys Gly His Leu Glu Arg Glu Cys Met Glu Glu Thr Cys Ser Tyr
        50                  55                  60

GAA GAG GCC CGC GAG GTC TTT GAG GAC AGC GAC AAG ACG AAT GAA TTC       240
Glu Glu Ala Arg Glu Val Phe Glu Asp Ser Asp Lys Thr Asn Glu Phe
 65                 70                  75                  80

TGG AAT AAA TAC AAA GAT GGC GAC CAG TGT GAG ACC AGT CCT TGC CAG       288
Trp Asn Lys Tyr Lys Asp Gly Asp Gln Cys Glu Thr Ser Pro Cys Gln
                85                  90                  95

AAC CAG GGC AAA TGT AAA GAC GGC CTC GGG GAA TAC ACC TGC ACC TGT       336
Asn Gln Gly Lys Cys Lys Asp Gly Leu Gly Glu Tyr Thr Cys Thr Cys
            100                 105                 110

TTA GAA GGA TTC GAA GGC AAA AAC TGT GAA TTA TTC ACA CGG AAG CTC       384
Leu Glu Gly Phe Glu Gly Lys Asn Cys Glu Leu Phe Thr Arg Lys Leu
        115                 120                 125

TGC AGC CTG GAC AAC GGG GAC TGT GAC CAG TTC TGC CAC GAG GAA CAG       432
Cys Ser Leu Asp Asn Gly Asp Cys Asp Gln Phe Cys His Glu Glu Gln
130                 135                 140

AAC TCT GTG GTG TGC TCC TGC GCC CGC GGG TAC ACC CTG GCT GAC AAC       480
Asn Ser Val Val Cys Ser Cys Ala Arg Gly Tyr Thr Leu Ala Asp Asn
145                 150                 155                 160

GGC AAG GCC TGC ATT CCC ACA GGG CCC TAC CCC TGT GGG AAA CAG ACC       528
Gly Lys Ala Cys Ile Pro Thr Gly Pro Tyr Pro Cys Gly Lys Gln Thr
                165                 170                 175

CTG GAA CGC AGG AAG AGG TCA GTG GCC CAG GCC ACC AGC AGC AGC GGG       576
Leu Glu Arg Arg Lys Arg Ser Val Ala Gln Ala Thr Ser Ser Ser Gly
            180                 185                 190

GAG GCC CCT GAC AGC ATC ACA TGG AAG CCA TAT GAT GCA GCC GAC CTG       624
Glu Ala Pro Asp Ser Ile Thr Trp Lys Pro Tyr Asp Ala Ala Asp Leu
        195                 200                 205

GAC CCC ACC GAG AAC CCC TTC GAC CTG CTT GAC TTC AAC CAG ACG CAG       672
Asp Pro Thr Glu Asn Pro Phe Asp Leu Leu Asp Phe Asn Gln Thr Gln
210                 215                 220

CCT GAG AGG GGC GAC AAC AAC CTC ACC AGG ATC GTG GGA GGC CAG GAA       720
Pro Glu Arg Gly Asp Asn Asn Leu Thr Arg Ile Val Gly Gly Gln Glu
225                 230                 235                 240

TGC AAG GAC GGG GAG TGT CCC TGG CAG GCC CTG CTC ATC AAT GAG GAA       768
Cys Lys Asp Gly Glu Cys Pro Trp Gln Ala Leu Leu Ile Asn Glu Glu
                245                 250                 255

AAC GAG GGT TTC TGT GGT GGA ACT ATT CTG AGC GAG TTC TAC ATC CTA       816
Asn Glu Gly Phe Cys Gly Gly Thr Ile Leu Ser Glu Phe Tyr Ile Leu
            260                 265                 270

ACG GCA GCC CAC TGT CTC TAC CAA GCC AAG AGA TTC AAG GTG AGG GTA       864
Thr Ala Ala His Cys Leu Tyr Gln Ala Lys Arg Phe Lys Val Arg Val
        275                 280                 285

GGG GAC CGG AAC ACG GAG CAG GAG GAG GGC GGT GAG GCG GTG CAC GAG       912
Gly Asp Arg Asn Thr Glu Gln Glu Glu Gly Gly Glu Ala Val His Glu
290                 295                 300

GTG GAG GTG GTC ATC AAG CAC AAC CGG TTC ACA AAG GAG ACC TAT GAC       960
Val Glu Val Val Ile Lys His Asn Arg Phe Thr Lys Glu Thr Tyr Asp
```

-continued

```
Val Glu Val Val Ile Lys His Asn Arg Phe Thr Lys Glu Thr Tyr Asp
305                 310                 315                 320

TTC GAC ATC GCC GTG CTC CGG CTC AAG ACC CCC ATC ACC TTC CGC ATG        1008
Phe Asp Ile Ala Val Leu Arg Leu Lys Thr Pro Ile Thr Phe Arg Met
                325                 330                 335

AAC GTG GCG CCT GCC TGC CTC CCC GAG CGT GAC TGG GCC GAG TCC ACG        1056
Asn Val Ala Pro Ala Cys Leu Pro Glu Arg Asp Trp Ala Glu Ser Thr
            340                 345                 350

CTG ATG ACG CAG AAG ACG GGG ATT GTG AGC GGC TTC GGG CGC ACC CAC        1104
Leu Met Thr Gln Lys Thr Gly Ile Val Ser Gly Phe Gly Arg Thr His
        355                 360                 365

GAG AAG GGC CGG CAG TCC ACC AGG CTC AAG ATG CTG GAG GTG CCC TAC        1152
Glu Lys Gly Arg Gln Ser Thr Arg Leu Lys Met Leu Glu Val Pro Tyr
    370                 375                 380

GTG GAC CGC AAC AGC TGC AAG CTG TCC AGC AGC TTC ATC ATC ACC CAG        1200
Val Asp Arg Asn Ser Cys Lys Leu Ser Ser Ser Phe Ile Ile Thr Gln
385                 390                 395                 400

AAC ATG TTC TGT GCC GGC TAC GAC ACC AAG CAG GAG GAT GCC TGC CAG        1248
Asn Met Phe Cys Ala Gly Tyr Asp Thr Lys Gln Glu Asp Ala Cys Gln
                405                 410                 415

GGG GAC AGC GGG GGC CCG CAC GTC ACC CGC TTC AAG GAC ACC TAC TTC        1296
Gly Asp Ser Gly Gly Pro His Val Thr Arg Phe Lys Asp Thr Tyr Phe
            420                 425                 430

GTG ACA GGC ATC GTC AGC TGG GGA GAG AGC TGT GCC CGT AAG GGG AAG        1344
Val Thr Gly Ile Val Ser Trp Gly Glu Ser Cys Ala Arg Lys Gly Lys
        435                 440                 445

TAC GGG ATC TAC ACC AAG GTC ACC GCC TTC CTC AAG TGG ATC GAC AGG        1392
Tyr Gly Ile Tyr Thr Lys Val Thr Ala Phe Leu Lys Trp Ile Asp Arg
    450                 455                 460

TCC ATG AAA ACC AGG GGC TTG CCC AAG GCC AAG AGC CAT GCC CCG GAG        1440
Ser Met Lys Thr Arg Gly Leu Pro Lys Ala Lys Ser His Ala Pro Glu
465                 470                 475                 480

GTC ATA ACG TCC TCT CCA TTA AAG TGA                                    1467
Val Ile Thr Ser Ser Pro Leu Lys
                485
```

(2) INFORMATION FOR SEQ ID NO: 44:

(i) SEQUENCE CHARACTERISTICS:
       (A) LENGTH: 488 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 44:

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
```

-continued

```
                100                 105                 110
Leu Glu Gly Phe Glu Gly Lys Asn Cys Glu Leu Phe Thr Arg Lys Leu
            115                 120                 125
Cys Ser Leu Asp Asn Gly Asp Cys Asp Gln Phe Cys His Glu Glu Gln
130                 135                 140
Asn Ser Val Val Cys Ser Cys Ala Arg Gly Tyr Thr Leu Ala Asp Asn
145                 150                 155                 160
Gly Lys Ala Cys Ile Pro Thr Gly Pro Tyr Pro Cys Gly Lys Gln Thr
                165                 170                 175
Leu Glu Arg Arg Lys Arg Ser Val Ala Gln Ala Thr Ser Ser Ser Gly
            180                 185                 190
Glu Ala Pro Asp Ser Ile Thr Trp Lys Pro Tyr Asp Ala Ala Asp Leu
            195                 200                 205
Asp Pro Thr Glu Asn Pro Phe Asp Leu Leu Asp Phe Asn Gln Thr Gln
        210                 215                 220
Pro Glu Arg Gly Asp Asn Asn Leu Thr Arg Ile Val Gly Gly Gln Glu
225                 230                 235                 240
Cys Lys Asp Gly Glu Cys Pro Trp Gln Ala Leu Leu Ile Asn Glu Glu
                245                 250                 255
Asn Glu Gly Phe Cys Gly Gly Thr Ile Leu Ser Glu Phe Tyr Ile Leu
            260                 265                 270
Thr Ala Ala His Cys Leu Tyr Gln Ala Lys Arg Phe Lys Val Arg Val
            275                 280                 285
Gly Asp Arg Asn Thr Glu Gln Glu Glu Gly Gly Glu Ala Val His Glu
        290                 295                 300
Val Glu Val Val Ile Lys His Asn Arg Phe Thr Lys Glu Thr Tyr Asp
305                 310                 315                 320
Phe Asp Ile Ala Val Leu Arg Leu Lys Thr Pro Ile Thr Phe Arg Met
                325                 330                 335
Asn Val Ala Pro Ala Cys Leu Pro Glu Arg Asp Trp Ala Glu Ser Thr
            340                 345                 350
Leu Met Thr Gln Lys Thr Gly Ile Val Ser Gly Phe Gly Arg Thr His
            355                 360                 365
Glu Lys Gly Arg Gln Ser Thr Arg Leu Lys Met Leu Glu Val Pro Tyr
        370                 375                 380
Val Asp Arg Asn Ser Cys Lys Leu Ser Ser Ser Phe Ile Ile Thr Gln
385                 390                 395                 400
Asn Met Phe Cys Ala Gly Tyr Asp Thr Lys Gln Glu Asp Ala Cys Gln
                405                 410                 415
Gly Asp Ser Gly Gly Pro His Val Thr Arg Phe Lys Asp Thr Tyr Phe
            420                 425                 430
Val Thr Gly Ile Val Ser Trp Gly Glu Ser Cys Ala Arg Lys Gly Lys
            435                 440                 445
Tyr Gly Ile Tyr Thr Lys Val Thr Ala Phe Leu Lys Trp Ile Asp Arg
        450                 455                 460
Ser Met Lys Thr Arg Gly Leu Pro Lys Ala Lys Ser His Ala Pro Glu
465                 470                 475                 480
Val Ile Thr Ser Ser Pro Leu Lys
                485
```

(2) INFORMATION FOR SEQ ID NO: 45:

(i) SEQUENCE CHARACTERISTICS:
        (A) LENGTH: 8 amino acids

```
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2...2
        (D) OTHER INFORMATION: Xaa = Arg, Asp, Phe, Thr, Leu or Ser (xi) SEQUENCE DESCRIPTION: SEQ ID NO: 45:

Gly Xaa Xaa Xaa Xaa Xaa Arg Xaa
1               5

(2) INFORMATION FOR SEQ ID NO: 46:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 46:

Gly Asp Asn Asn Leu Thr Arg Ile
1               5

(2) INFORMATION FOR SEQ ID NO: 47:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Gly Asp Gln Asn Leu Thr Arg Ile
1               5

(2) INFORMATION FOR SEQ ID NO: 48:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Gly Lys Asn Asn Leu Thr Arg Ile
1               5

(2) INFORMATION FOR SEQ ID NO: 49:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Gly Lys Gln Asn Leu Thr Arg Ile
1               5
```

(2) INFORMATION FOR SEQ ID NO: 50:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Gly Phe Asn Asp Phe Thr Arg Val
 1               5

(2) INFORMATION FOR SEQ ID NO: 51:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Gly Phe Gln Asp Phe Thr Arg Val
 1               5

(2) INFORMATION FOR SEQ ID NO: 52:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Gly Lys Asn Asp Phe Thr Arg Val
 1               5

(2) INFORMATION FOR SEQ ID NO: 53:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

Gly Lys Gln Asp Phe Thr Arg Val
 1               5

(2) INFORMATION FOR SEQ ID NO: 54:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 54:

Gly Phe Asn Asp Phe Thr Arg Ile

-continued

```
1               5
```

(2) INFORMATION FOR SEQ ID NO: 55:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

```
Gly Phe Gln Asp Phe Thr Arg Ile
1               5
```

(2) INFORMATION FOR SEQ ID NO: 56:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

```
Gly Lys Asn Asp Phe Thr Arg Ile
1               5
```

(2) INFORMATION FOR SEQ ID NO: 57:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

```
Gly Lys Gln Asp Phe Thr Arg Ile
1               5
```

(2) INFORMATION FOR SEQ ID NO: 58:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8...8
        (D) OTHER INFORMATION: Xaa = Ile or Val (xi) SEQUENCE DESCRIPTION: SEQ ID NO: 58:

```
Gly Thr Lys Ile Lys Pro Arg Xaa
1               5
```

(2) INFORMATION FOR SEQ ID NO: 59:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
    (ii) MOLECULE TYPE: peptide (ix) FEATURE:
         (A) NAME/KEY: Modified-site
         (B) LOCATION: 8...8
         (D) OTHER INFORMATION: Xaa = Ile or Val (xi) SEQUENCE DESCRIPTION: SEQ ID NO: 59:

Gly Thr Gln Ile Lys Pro Arg Xaa
1               5

(2) INFORMATION FOR SEQ ID NO: 60:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: 8...8
         (D) OTHER INFORMATION: Xaa = Ile or Val (xi) SEQUENCE DESCRIPTION: SEQ ID NO: 60:

Gly Lys Lys Ile Lys Pro Arg Xaa
1               5

(2) INFORMATION FOR SEQ ID NO: 61:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: 8...8
         (D) OTHER INFORMATION: Xaa = Ile or Val (xi) SEQUENCE DESCRIPTION: SEQ ID NO: 61:

Gly Lys Gln Ile Lys Pro Arg Xaa
1               5

(2) INFORMATION FOR SEQ ID NO: 62:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 62:

Gly Thr Lys Thr Ser Thr Arg Ile
1               5

(2) INFORMATION FOR SEQ ID NO: 63:

(i) SEQUENCE CHARACTERISTICS:
         (A) LENGTH: 8 amino acids
         (B) TYPE: amino acid
         (C) STRANDEDNESS: single
         (D) TOPOLOGY: linear
```

(ii) MOLECULE TYPE: peptide (xi) SEQUENCE DESCRIPTION: SEQ ID NO: 63:

Gly Thr Gln Thr Ser Thr Arg Ile
1               5

(2) INFORMATION FOR SEQ ID NO: 64:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 64:

Gly Lys Lys Thr Ser Thr Arg Ile
1               5

(2) INFORMATION FOR SEQ ID NO: 65:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 65:

Gly Lys Gln Thr Ser Thr Arg Ile
1               5

(2) INFORMATION FOR SEQ ID NO: 66:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Modified-site
           (B) LOCATION: 8...8
           (D) OTHER INFORMATION: Xaa = Ile or Val (xi) SEQUENCE DESCRIPTION: SEQ ID NO: 66:

Gly Leu Ser Ser Met Thr Arg Xaa
1               5

(2) INFORMATION FOR SEQ ID NO: 67:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Modified-site
           (B) LOCATION: 8...8
           (D) OTHER INFORMATION: Xaa = Ile or Val (xi) SEQUENCE DESCRIPTION: SEQ ID NO: 67:

```
Gly Leu Gln Ser Met Thr Arg Xaa
 1               5
```

(2) INFORMATION FOR SEQ ID NO: 68:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8...8
        (D) OTHER INFORMATION: Xaa = Ile or Val (xi) SEQUENCE DESCRIPTION: SEQ ID NO: 68:

```
Gly Lys Ser Ser Met Thr Arg Xaa
 1               5
```

(2) INFORMATION FOR SEQ ID NO: 69:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8...8
        (D) OTHER INFORMATION: Xaa = Ile or Val (xi) SEQUENCE DESCRIPTION: SEQ ID NO: 69:

```
Gly Lys Gln Ser Met Thr Arg Xaa
 1               5
```

(2) INFORMATION FOR SEQ ID NO: 70:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 70:

```
Gly Ser Lys Pro Gln Gly Arg Ile
 1               5
```

(2) INFORMATION FOR SEQ ID NO: 71:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

```
Gly Ser Gln Pro Gln Gly Arg Ile
 1               5
```

(2) INFORMATION FOR SEQ ID NO: 72:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

Gly Lys Lys Pro Gln Gly Arg Ile
1               5

(2) INFORMATION FOR SEQ ID NO: 73:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

Gly Lys Gln Pro Gln Gly Arg Ile
1               5

(2) INFORMATION FOR SEQ ID NO: 74:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

Gly Lys Gln Ile Glu Gly Arg Ile
1               5

(2) INFORMATION FOR SEQ ID NO: 75:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

Gly Lys Gln Met Lys Thr Arg Ile
1               5

(2) INFORMATION FOR SEQ ID NO: 76:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 76:

Gly Leu Glu Arg Arg Lys Arg Ile
1               5

(2) INFORMATION FOR SEQ ID NO: 77:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 77:

Gly Leu Gln Arg Arg Lys Arg Ile
1               5

(2) INFORMATION FOR SEQ ID NO: 78:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 78:

Gly Lys Glu Arg Arg Lys Arg Ile
1               5

(2) INFORMATION FOR SEQ ID NO: 79:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 79:

Gly Lys Gln Arg Arg Lys Arg Ile
1               5

(2) INFORMATION FOR SEQ ID NO: 80:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

Gly Leu Ala Arg Val Thr Arg Ile
1               5

(2) INFORMATION FOR SEQ ID NO: 81:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

Gly Leu Gln Arg Val Thr Arg Ile
1               5

(2) INFORMATION FOR SEQ ID NO: 82:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

Gly Lys Ala Arg Val Thr Arg Ile
1               5

(2) INFORMATION FOR SEQ ID NO: 83:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Gly Lys Gln Arg Val Thr Arg Ile
1               5

(2) INFORMATION FOR SEQ ID NO: 84:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 84:

Gly Leu Gln Arg Val Arg Arg Ile
1               5

(2) INFORMATION FOR SEQ ID NO: 85:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

Gly Lys Gln Arg Val Arg Arg Ile
1               5

(2) INFORMATION FOR SEQ ID NO: 86:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Gly Leu His Arg Arg Arg Arg Ile
1               5

(2) INFORMATION FOR SEQ ID NO: 87:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Gly Leu Gln Arg Arg Arg Arg Ile
1               5

(2) INFORMATION FOR SEQ ID NO: 88:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

Gly Lys His Arg Arg Arg Arg Ile
1               5

(2) INFORMATION FOR SEQ ID NO: 89:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

Gly Lys Gln Arg Arg Arg Arg Ile
1               5

(2) INFORMATION FOR SEQ ID NO: 90:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

Gly Leu Asn Arg Pro Lys Arg Ile
1               5

(2) INFORMATION FOR SEQ ID NO: 91:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 91:

Gly Leu Gln Arg Pro Lys Arg Ile

```
1               5
```

(2) INFORMATION FOR SEQ ID NO: 92:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

```
Gly Lys Asn Arg Pro Lys Arg Ile
1               5
```

(2) INFORMATION FOR SEQ ID NO: 93:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

```
Gly Lys Gln Arg Pro Lys Arg Ile
1               5
```

(2) INFORMATION FOR SEQ ID NO: 94:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

```
Gly Leu Arg Ile Arg Lys Arg Ile
1               5
```

(2) INFORMATION FOR SEQ ID NO: 95:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

```
Gly Leu Gln Ile Arg Lys Arg Ile
1               5
```

(2) INFORMATION FOR SEQ ID NO: 96:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 96:

```
Gly Lys Arg Ile Arg Lys Arg Ile
 1               5
```

(2) INFORMATION FOR SEQ ID NO: 97:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 97:

```
Gly Lys Gln Ile Arg Lys Arg Ile
 1               5
```

(2) INFORMATION FOR SEQ ID NO: 98:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

```
Gly Lys Gln Arg Ser Lys Arg Ile
 1               5
```

(2) INFORMATION FOR SEQ ID NO: 99:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 99:

```
Gly Lys Gln Arg Val Thr Arg Ile
 1               5
```

(2) INFORMATION FOR SEQ ID NO: 100:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 100:

```
Gly Lys Gln Arg Leu Lys Arg Ile
 1               5
```

(2) INFORMATION FOR SEQ ID NO: 101:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 101:

Arg Val Thr Arg Ile
1               5

(2) INFORMATION FOR SEQ ID NO: 102:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 102:

Thr Lys Glu Arg Arg Lys Arg Ser Val Ala
1               5                   10

(2) INFORMATION FOR SEQ ID NO: 103:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 103:

Asn Leu Thr Arg Ile Val Gly Gly
1               5

(2) INFORMATION FOR SEQ ID NO: 104:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 104:

Asp Phe Thr Arg Val Val Gly Gly
1               5

(2) INFORMATION FOR SEQ ID NO: 105:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

Thr Leu Glu Arg Thr Val Gly Gly
1               5

(2) INFORMATION FOR SEQ ID NO: 106:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 106:

Ile Lys Pro Arg Ile Val Gly Gly
1               5

(2) INFORMATION FOR SEQ ID NO: 107:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

Ser Met Thr Arg Ile Val Gly Gly
1               5

(2) INFORMATION FOR SEQ ID NO: 108:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 108:

Met Lys Thr Arg Ile Val Gly Gly
1               5

(2) INFORMATION FOR SEQ ID NO: 109:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

Ile Glu Gly Arg Ile Val Gly Gly
1               5

(2) INFORMATION FOR SEQ ID NO: 110:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 110:

Arg Arg Lys Arg Ile Val Gly Gly
1               5

(2) INFORMATION FOR SEQ ID NO: 111:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

Arg Val Arg Arg Ile Val Gly Gly
1               5

(2) INFORMATION FOR SEQ ID NO: 112:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 112:

Arg Arg Arg Arg Ile Val Gly Gly
1               5

(2) INFORMATION FOR SEQ ID NO: 113:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 113:

Arg Pro Lys Arg Ile Val Gly Gly
1               5

(2) INFORMATION FOR SEQ ID NO: 114:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 114:

Ile Arg Lys Arg Ile Val Gly Gly
1               5

(2) INFORMATION FOR SEQ ID NO: 115:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 115:

Arg Ser Lys Arg Ile Val Gly Gly
1               5

(2) INFORMATION FOR SEQ ID NO: 116:

(i) SEQUENCE CHARACTERISTICS:
      (A) LENGTH: 8 amino acids
      (B) TYPE: amino acid
      (C) STRANDEDNESS: single
      (D) TOPOLOGY: linear

```
        (ii) MOLECULE TYPE: peptide (xi) SEQUENCE DESCRIPTION: SEQ ID NO: 116:

Arg Val Thr Arg Ile Val Gly Gly
  1               5

(2) INFORMATION FOR SEQ ID NO: 117:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 117:

Arg Leu Lys Arg Ile Val Gly Gly
  1               5

(2) INFORMATION FOR SEQ ID NO: 118:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 118:

Pro Gln Gly Arg Ile Val Gly Gly
  1               5

(2) INFORMATION FOR SEQ ID NO: 119:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 119:

Thr Ser Thr Arg Ile Val Gly Gly
  1               5

(2) INFORMATION FOR SEQ ID NO: 120:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 120:

Met Lys Thr Arg
  1

(2) INFORMATION FOR SEQ ID NO: 121:

(i) SEQUENCE CHARACTERISTICS:
            (A) LENGTH: 8 amino acids
            (B) TYPE: amino acid
            (C) STRANDEDNESS: single
            (D) TOPOLOGY: linear
```

(ii) MOLECULE TYPE: peptide (xi) SEQUENCE DESCRIPTION: SEQ ID NO: 121:

Xaa Xaa Xaa Arg Xaa Val Gly Gly
1               5

(2) INFORMATION FOR SEQ ID NO: 122:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 122:

Met Lys Thr Lys Gly
1               5

(2) INFORMATION FOR SEQ ID NO: 123:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 123:

Gly Glu Ser Leu Phe Ile Arg Arg Glu Gln
1               5                   10

(2) INFORMATION FOR SEQ ID NO: 124:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 124:

Ile Leu Ala Arg Val Thr Arg Ala Asn Ser Phe Leu Glu Glu
1               5                   10

(2) INFORMATION FOR SEQ ID NO: 125:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 125:

Ser Val Ala Gln Ala Thr Ser
1               5

(2) INFORMATION FOR SEQ ID NO: 126:

(i) SEQUENCE CHARACTERISTICS:
        (A) LENGTH: 7 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 126:

Leu Phe Ile Arg Arg Glu Gln
1               5

(2) INFORMATION FOR SEQ ID NO: 127:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 127:

Ala Asn Ser Phe Leu Glu Glu
1               5

(2) INFORMATION FOR SEQ ID NO: 128:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 128:

Val Thr Arg Ala Asn Ser Phe Leu Glu Glu
1               5                   10

(2) INFORMATION FOR SEQ ID NO: 129:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 129:

Arg Val Thr Arg Ala
1               5

(2) INFORMATION FOR SEQ ID NO: 130:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 130:

Arg Arg Lys Arg Ser
1               5

(2) INFORMATION FOR SEQ ID NO: 131:

(i) SEQUENCE CHARACTERISTICS:
        (A) LENGTH: 5 amino acids
        (B) TYPE: amino acid (C) STRANDEDNESS: single
            (D) TOPOLOGY: linear (ii) MOLECULE TYPE: peptide (ix) FEATURE:
            (A) NAME/KEY: Modified-site
            (B) LOCATION: 3...3
            (D) OTHER INFORMATION: Xaa = Lys or Arg (xi) SEQUENCE DESCRIPTION: SEQ ID NO: 131:

Arg Xaa Xaa Arg Xaa
 1               5

(2) INFORMATION FOR SEQ ID NO: 132:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 132:

Asp Phe Thr Arg Val
 1               5

(2) INFORMATION FOR SEQ ID NO: 133:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 133:

Ile Lys Pro Arg Ile
 1               5

(2) INFORMATION FOR SEQ ID NO: 134:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 134:

Ser Met Thr Arg Ile
 1               5

(2) INFORMATION FOR SEQ ID NO: 135:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 135:

Met Lys Thr Arg Ile
 1               5

(2) INFORMATION FOR SEQ ID NO: 136:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 136:

Ile Glu Gly Arg Ile
1            5

(2) INFORMATION FOR SEQ ID NO: 137:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 137:

Arg Arg Lys Arg Ile
1            5

(2) INFORMATION FOR SEQ ID NO: 138:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 138:

Arg Val Arg Arg Ile
1            5

(2) INFORMATION FOR SEQ ID NO: 139:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

Arg Arg Arg Arg Ile
1            5

(2) INFORMATION FOR SEQ ID NO: 140:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 140:

Arg Pro Lys Arg Ile
1            5

(2) INFORMATION FOR SEQ ID NO: 141:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 141:

Ile Arg Lys Arg Ile
1               5

(2) INFORMATION FOR SEQ ID NO: 142:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 142:

Arg Ser Lys Arg Ile
1               5

(2) INFORMATION FOR SEQ ID NO: 143:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 143:

Arg Leu Lys Arg Ile
1               5

(2) INFORMATION FOR SEQ ID NO: 144:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 144:

Pro Gln Gly Arg Ile
1               5

(2) INFORMATION FOR SEQ ID NO: 145:

(i) SEQUENCE CHARACTERISTICS:
        (A) LENGTH: 5 amino acids
        (B) TYPE: amino acid
        (C) STRANDEDNESS: single
        (D) TOPOLOGY: linear -continued

```
    (ii) MOLECULE TYPE: peptide (xi) SEQUENCE DESCRIPTION: SEQ ID NO: 145:

Thr Ser Thr Arg Ile
1               5
```

FACTOR X DELETION MUTANTS AND ANALOGUES THEREOF

CROSS-REFERENCES TO RELATED APPLICATIONS

This application is the U.S. national phase of PCT/AT98/00046, filed Feb. 27, 1998, which claims priority to Austrian Application A336/97, filed Feb. 27, 1997.

FIELD OF THE INVENTION

The invention relates to factor XΔ analogues having a deletion of the amino acids from Arg180 to Arg234 and a modification in the region of the amino acid sequence between Gly173 and Arg179, to preparations containing the factor XΔ analogues or factor Xa analogues according to the invention, as well as to methods of preparing the factor XΔ analogues according to the invention.

BACKGROUND OF INVENTION

After the blood coagulation process has been initiated, the coagulation cascade continues through sequential activation of various proenzymes (zymogens) in the blood to their active forms, the serine proteases. Among them are, inter alia, factor XII/XIIa, factor XI/XIa, factor IX/IXa, factor., X/Xa, factor VII/VIIa and prothrombin/thrombin. In their physiological state, most of these enzymes are only active if associated to a membrane surface in a complex. Ca ions are involved in many of these processes. The blood coagulation will either follow the intrinsic pathway, wherein all protein components are present in the blood, or the extrinsic pathway, wherein the tissue factor plays a critical role. Finally, the wound will close by thrombin cleaving fibrinogen to fibrin.

The prothrombinase complex is responsible for activating prothrombin to thrombin. Thrombin is an important enzyme which can act as a procoagulant as well as an anticoagulant. The prothrombinase complex, in which, inter alia, factor Va (as cofactor) and factor Xa (as serine protease) are involved, assembles in a Ca-dependent association at the surface of phospholipids. It is discussed that factor Xa is the catalytic component of the prothrombinase complex.

Factor X (Stuart-Prower factor) is a vitamin K-dependent coagulation glycoprotein which can be activated by the intrinsic and the extrinsic blood coagulation cascade. The primary translation product of factor X (pre-pro-FX) has 488 amino acids and is synthesized by the liver or human hepatoma cells initially as a single chain 75 kD precursor protein. In plasma, factor X is largely present as a double chain molecule (Fair et al., 1984, Blood 64:194–204).

During biosynthesis, after cleavage of the pre-sequence by a signal peptidase (between Ser23/Leu24) and of the propeptide (between Arg40/Ala41), the single chain factor X molecule is cleaved by processing and removal of the tripeptide Arg180-Lys181-Arg182 to the double chain form consisting of the approximately 22 kD light chain and the approximately 50 kD heavy chain, which are connected via a disulfide bridge (FIG. 2A, Panel 1A). Therefore, factor X circulates in the plasma as a double chain molecule.

During the blood coagulation process, factor X is converted from inactive zymogen to active protease factor Xa by limited proteolysis, wherein factor X can be activated to factor Xa in either of two membrane-associated complexes: in the extrinsic factor VIIa-tissue factor complex or in the intrinsic factor VIIIa-factor IXa-phospholipid-Ca complex, or "tenase complex" (Mertens et al., 1980, Biochem. J. 185:647–658). A proteolytic cleavage between amino acids Arg234/Ile235 results in the release of an activation peptide having a length of 52 amino acids from the N-terminus of the heavy chain and thus to the formation of the active enzyme, factor Xa. The catalytic center of factor Xa is located on the heavy chain.

Activation via the factor VIIa-TF (extrinsic) complex results in the formation of Factor Xaα (35 kD) and factor Xaβ (31 kD), with a polypeptide of 42 (kD) forming, too, if the factor VIIa,concentration in the complex is low. Factor Xaα is formed by a cleavage at Arg234/Ile235 of the heavy chain and represents the activation of factor X to factor Xa. The occurence of factor Xaβ presumably results from an autocatalytic cleavage at Arg469/Gly470 in the C-terminus of the heavy chain of factor Xaα and the cleavage of a 4.5 kD peptide. Like factor Xaα, factor Xaβ has catalytic activity. It has been shown, however, that a plasminogen receptor binding site is formed by the cleavage of factor Xaα to factor Xaβ, and that factor Xaβ optionally has fibrinolytic activity or is involved in fibrinolysis as a cofactor. The transformation of factor Xaα to factor Xaβ, however, is slower than the formation of thrombin, thus preventing the initiation of fibrinolysis before a blood clot is formed (Pryzdial et al., 1996, J. Biol. Chem. 271:16614–16620; Pryzdial et al., 1996, J. Biol. Chem. 271:16621–16626).

The 42 kD polypeptide results from processing in the C-terminus of the heavy chain between Arg469/Gly470 without previous processing between Arg234/Ile235. Like a factor Xaγ fragment formed by proteolysis at Lys370, this intermediate has no catalytic activity (Mertens et al., 1980, Biochem. J. 185:647–658; Pryzdial et al., 1996, J. Biol. Chem. 271:16614–16620).

Intrinsic factor X activation is catalysed by the factor IXa-factor VIIIa complex. The same processing products are obtained during activation, but the factor Xaβ product is obtained in a larger quantity than other factor X processing products (Jesty et al., 1974, J. Biol. Chem. 249:5614).

In vitro, factor X can, for instance, be activated by Russell's viper venom (RVV) or trypsin (Bajaj et al., 1973, J. Biol. Chem. 248:7729–7741) or by purified physiological activators, such as FVIIa/TF complex or factor IXa/factor VIIIa complex (Mertens et al., 1980, Biochem. J. 185:647–658).

Most commercially available factor X products from plasma contain a mixture of factor Xaα and factor Xaβ, because after activation of factor X to factor Xa mainly factor Xaα is formed, which is, in turn, cleaved to factor Xaβ in an autocatalytic process.

In order to produce a uniform factor Xa product having high molecular integrity, EP 0 651 054 suggested to activate factor X with RVV over an extended period of time so that the resulting final product substantially contains factor Xaβ. The by-products, e.g. factor Xaα, as well as the protease were subsequently removed by several chromatographic steps.

cDNA for factor X has been isolated and characterized (Leytus et al., 1984, Proc. Natl. Acad. Sci., U.S.A., 82:3699–3702; Fung et al., 1985, Proc. Natl. Acad. Sci., U.S.A., 82:3591–3595). Human factor X has been expressed in vitro in various types of cells, such as human embryonal renal cells or CHO cells (Rudolph et al., 1997, Prot. Expr. Purif. 10:373–378, Wolf et al., 1991, J. Biol. Chem. 266:13726–13730). However, it was found that in the recombinant expression of human factor X, the processing at position Arg40/Ala41 is inefficient, as opposed to the situation in viva, and that different N-termini form at the light chain of factor X (Wolf et al., 1991, J. Biol. Chem. 266:13726–13730). Recombinant factor X (rFX) was activated to rfactor Xa (rFXa) by RVV in vitro, or rFXa was expressed directly, with the activation peptide being deleted from amino acid 183 to amino acid 234 and replaced by a tripeptide in order to allow processing directly to a double chain rFXa form. About 70% of purified rFX was processed to light and heavy chain, while the remaining 300 represented single chain rFX of 75 kD. Direct expression of rFXa did result in the formation of active factor Xa, but also of inactive intermediates. Furthermore, Wolf et al. (1991, J. Biol. Chem. 266:13726–13730) detected still reduced activity of recombinant factor X, which they ascribed to the poorer ability of rFX to be activated by RVV and to the inactive protein and polypeptide populations of the single chain precursor molecule. In particular, they found high rFXa instability when expressed by recombinant cells, which they ascribed to the high rate of autoproteolysis.

In order to study the function of the C-terminal peptide of factor Xaα, Eby et al. (1992, Blood 80 (suppl. 1): 1214 A) introduced a stop codon at position Gly430 of the factor X sequence. However, they did not find a difference between the rate of activation of factor Xa (Fxaα) with β-peptide or a deletion mutant without β-peptide (FXaβ).

Factor Xa is an important component of the prothrombinase complex and is therefore under discussion as a primary mediator for quick hemostasis, and thus it seems suitable for the treatment of patients suffering from blood coagulation disorders, e.g. hemophilia.

Particularly the treatment of hemophilia patients suffering from factor VIII or factor IX deficiency with factor concentrates produced from plasma is often complicated by the formation of inhibiting antibodies against these factors in long-term therapy. Therefore, a number of alternatives have been developed to treat hemophiliacs with factors having bypass activity. The use of prothrombin complex concentrate, partially activated prothrombinase complex (APPC), factor VIIa or FEIBA has been suggested. Commercial preparations having factor VIII bypass activity (FEIBA) are, for instance, FEIBA® or Autoplex®. FEIBA, contains comparable units of factor II, factor VII, factor IX, factor X and FEIBA, small amounts of factor VIII and factor V, and traces of activated coagulation factors, such as thrombin and factor Xa or a factor having factor X-like activity (Elsinger, 1982, Activated Prothrombin Complex Concentrates. Ed. Mariani, Russo, Mandelli, pp. 77–87). Elsinger particularly points at the importance of a "factor Xa-like" activity in FEIBA. Factor VIII bypass activity was shown by Giles et al (1988, British J. Haematology 9:491–497) for a combination of purified factor Xa and phospholipids in an animal model.

Therefore, factor X/Xa or factor X/Xa-like proteins, either alone or as a component of a coagulation complex, are in high demand and can be used in various fields of application in hemostasis therapy.

In vivo as well as in vitro, the half-life of factor Xa is considerably shorter than the half-life of the zymogen. For instance, factor X can be stored stably in glycerol for 18 months, while factor Xa is stable for only 5 months under the same conditions (Bajaj et al., 1973, J. Biol. Chem. 248:7729–7741) and shows reduced activity by more than 60% after 8 months in glycerol at 4° C. (Teng et al., 1981, Thrombosis Res. 22:213–220). The half-life of factor Xa in serum is a mere 30 seconds.

Because factor X is instable, the administration of factor X preparations has been suggested (U.S. Pat. No. 4,501, 731). If, however, the bleeding is so serious that the patient might die, particularly in a hemophiliac, the administration of factor X is ineffective, because owing to the functional "tenase complex" deficiency in the intrinsic pathway of blood coagulation, factor X can not be sufficiently activated to factor Xa, and activation via the extrinsic pathway is often too slow to show effects quickly. Moreover, hemophiliacs have sufficient amounts of factor X, but its prothrombinase activity is 1000 times less than that of factor Xa. In such cases it is necessary to administer activated factor Xa directly, optionally in combination with phospholipids, as described in Giles et al. (1988, British J. Haematology 9:491–497) or with other coagulation factors, e.g. with factor VIII bypass activity.

In the preparation of factor Xa from factor X, activation so far mostly has been carried out by non-physiological activators of animal origin, such as RVV or trypsin, and it was necessary to make absolutely sure that the final product is completely free of these proteases. As mentioned above, when factor X is activated to factor Xa, quite a number of intermediates, some of them inactive, are formed (Bajaj et al., 1973, J. Bio. Chem. 248:7729–7741; Mertens et al., 1980, Biochem. J. 185:647–658). The presence of such intermediates results in reduced specific activity of the product and may produce intermediates which can function as active serine protease antagonists. Therefore, the.preparation of a uniform, pure product having high specific activity according to conventional methods requires complex processes of activation and chromatographic purification.

SUMMARY OF INVENTION

Thus, the aim of the present invention is to provide a preparation containing a polypeptide having factor X/Xa activity which exhibits high stability and can be activated to factor Xa without using any of the usual proteases, particularly those of animal origin, such as, for instance, RVV or trypsin. Another aim is to provide a pharmaceutical preparation having factor VIII bypass activity.

According to the present invention, the aim is reached by providing a factor X analogue having a deletion of the amino acids Arg180 to Arg234 of the factor X amino acid sequence and a modification of this factor X deletion mutant in the region of the amino acid sequence between Gly173 and Arg179. By the deletion of the amino acid sequence from Arg180 to Arg234, the tripeptide Arg180 to Arg182 as well as the activation peptide Ser183 to Arg234 are deleted, and the light and heavy chains of factor X and the amino acids Arg179 and Ile235 are directly fused. This fusion sequence, however, does not contain a natural cleavage site for a protease. By modifying the region of the factor X sequence between amino acid Gly173 and Arg179 and optionally of Ile235, a factor X deletion mutant according to the present invention is obtained, which has a novel detection and processing site not occurring at this position in the polypeptide for a protease which would not usually cleave the polypeptide at this position. Said modification is, at least, an exchange of at least one amino acid between position Gly173 and Arg179 and, optionally of Ile235 of the factor X amino acid sequence. The position of amino acids refers to the numbering according to the sequence presented in FIGS. 1A and 1B, starting with Met1 and ending with Lys488. In order to simplify the nomenclature, the amino acid numbering given for the complete factor X sequence is adhered to for the modified factor X deletion mutant according to the present invention, but said modified factor X deletion mutant will hereinafter be referred to as factor XΔ analogue.

Said modification can be a substitution of at least one amino acid, or an insertion of a peptide sequence representing a protease recognition or cleavage site. In the factor XΔ analogue according to the present invention, the modification is preferably such that it represents a recognition and cleavage sequence for a protease from the group of endoproteases, such as kexin/Kex2, furin/PACE, PC1/PC3, PC2, PC4, PACE 4, LPC/PC7 (as described in Barr et al., 1991, Cell 66:1–3 or in U.S. Pat. No. 5,460,950), serine proteases, such as factor IIa, factor VIIa, factor IXa, factor XIIa, factor XIa, factor Xa, or kallikrein, or a derivative of these proteases.

Preferably, said modification is selected such that processing by one of these proteases leads to a polypeptide corresponding to native factor Xa in its biological activity and displaying factor Xa activity. For optimal processing, it may be necessary in individual cases to exchange the amino acid Ile235, too. Preferably, however, the NH$_2$-terminal amino acid isoleucine of the heavy chain should still be maintained after activation, because isoleucine represents one of those amino acids which perform an essential function in the formation of the substrate binding pocket (Watzke. et al., 1995, Molecular Basis of Thrombosis and Hemostasis, ed. Katherine High & Harold Roberts). The factor XΔ analogues according to the present invention display a structural difference, particularly on the amino acid level, as compared to a native factor X sequence, but after activation their activity is comparable to that of naturally occurring factor X or factor Xa, respectively.

BRIEF DESCRIPTION OF DRAWINGS

FIGS. 1A and 1B show the nucleotide and amino acid sequence of factor X (SEQ ID NOS:43 and 44, respectively).

DETAILED DESCRIPTION

The invention exemplary provides a number of factor XΔ analogues having a deletion and, in addition, a modification between Gly173 and Arg179 and optionally of Ile235. Modifications can be at one or more positions in the region between amino acids Gly173 and Arg179, and optionally Ile235, based on the factor X sequence numbered from Met1 to Lys488 according to FIGS. 1A and 1B. Amino acid substitutions can be at positions Ile235 (R1), Arg179, Glu178 (R2), Leu177 (R3), Thr176 (R4), Gln175 (R5) and Lys174 (R6), with Arg179, however preferably remaining unchanged.

Preferably, the factor XΔ analogues according to the invention contain a factor X sequence with Gly173-R6-R5-R4-R3-R2-Arg179-R1 (SEQ ID NO:45), wherein R1=Ile, Val, Ala, Ser or Thr; R2=Glu, Thr, Pro, Gly, Lys or Arg; R3=Leu, Phe, Lys, Met, Gln, Ser, Val, Arg or Pro; R4=Thr, Asn, Asp, Ile, Ser, Met, Pro, Arg or Lys; R5=Asn, Lys, Ser, Glu, Gln, Ala, His or Arg; and R6=Arg, Asp, Phe, Thr, Leu or Ser.

Preferred embodiments of the factor X analogues according to the invention are factor X analogues having a modification with a) R1=Ile, R2=Thr, R3=Leu, R4=Asn and optionally R5=Asn and/or R6=Asp (SEQ ID NOS:46–49), and processed by factor VIIa or factor IXa;

b) R1=Val, R2=Thr, R3=Phe, R4=Asp, and optionally R5=Asn and/or R6=Phe and/or R1=Ile or Val (SEQ ID NOS:50–57) (FIG. 2A, panel A), and processed by factor XIa;

c) R1=Ile or Val, R2=Pro, R3=Lys, R4=Ile, and optionally R5=Lys and/or R6=Thr (SEQ ID NOS:58–61) (FIG. 2A, panel C), or R1=Ile, R2=Thr, R3=Ser, R4=Thr, and optionally R5=Lys and/or R6=Thr (SEQ ID NOS:62–65) (FIG. 2A, panel I), and processed by factor XIIa;

d) R1=Ile or Val, R2=Thr, R3=Met, R4=Ser, and optionally R5=Ser and/or R6=Leu (SEQ ID NOS:66–69) (FIG. 2A, panel D), and processed by kallikrein;

e) R1=Ile, R2=Gly, R3=Gln, R4=Pro, and optionally R5=Lys and/or R6=Ser (SEQ ID NOS:70–73) (FIG. 2A, panel H), or R1=Ile, R2=Gly, R3=Glu, R4=Ile (SEQ ID NO:74) (FIG. 2A, panel F), or R1=Ile, R2=Thr, R3=Lys, R4=Met (SEQ ID NO:75) (FIG. 2A, panel E), and processed by factor Xa;

f) R1=Ile, R2=Lys, R3=Arg, R4=Arg, and optionally R5=Glu and/or R6=Leu (SEQ ID NOS:76–79), or R1=Ile, R2=Thr, R3=Val, R4=Arg, and optionally R5=Ala and/or R6=Leu (SEQ ID NOS:80–83), or R1=Ile, R2=Arg, R3=Val, R4=Arg, and optionally R5=Gln and/or R6=Leu (SEQ ID NOS:84 and 85), or R1=Ile, R2=Arg, R3=Arg, R4=Arg, and optionally R5=His and/or R6=Leu (SEQ ID NOS:86–89), or R1=Ile, R2=Lys, R3=Pro, R4=Arg, and optionally R5=Asn and/or R6=Leu (SEQ ID NOS:90–93), or R1=Ile, R2=Lys, R3=Arg, R4=Ile, and optionally R5=Arg and/or R6=Leu (SEQ ID NO:94–97), or R1=Ile, R2=Lys, R3=Ser, and R4=Arg (SEQ ID NO:98), or R1=Ile, R2=Thr, R3=Val, and R4=Arg (SEQ ID NO:99), or R1=Ile, R2=Lys, R3=Leu, and R4=Arg (SEQ ID NO:100) (all see FIG. 2A, panel G), with the sequences mentioned under f) being processed by a dibasic endoprotease, such as kexin/Kex2, furin/PACE, PC1/PC3, PC2, PC4, PACE 4, LPC/PC7, or a derivative of one of these proteases.

Figure 2A:
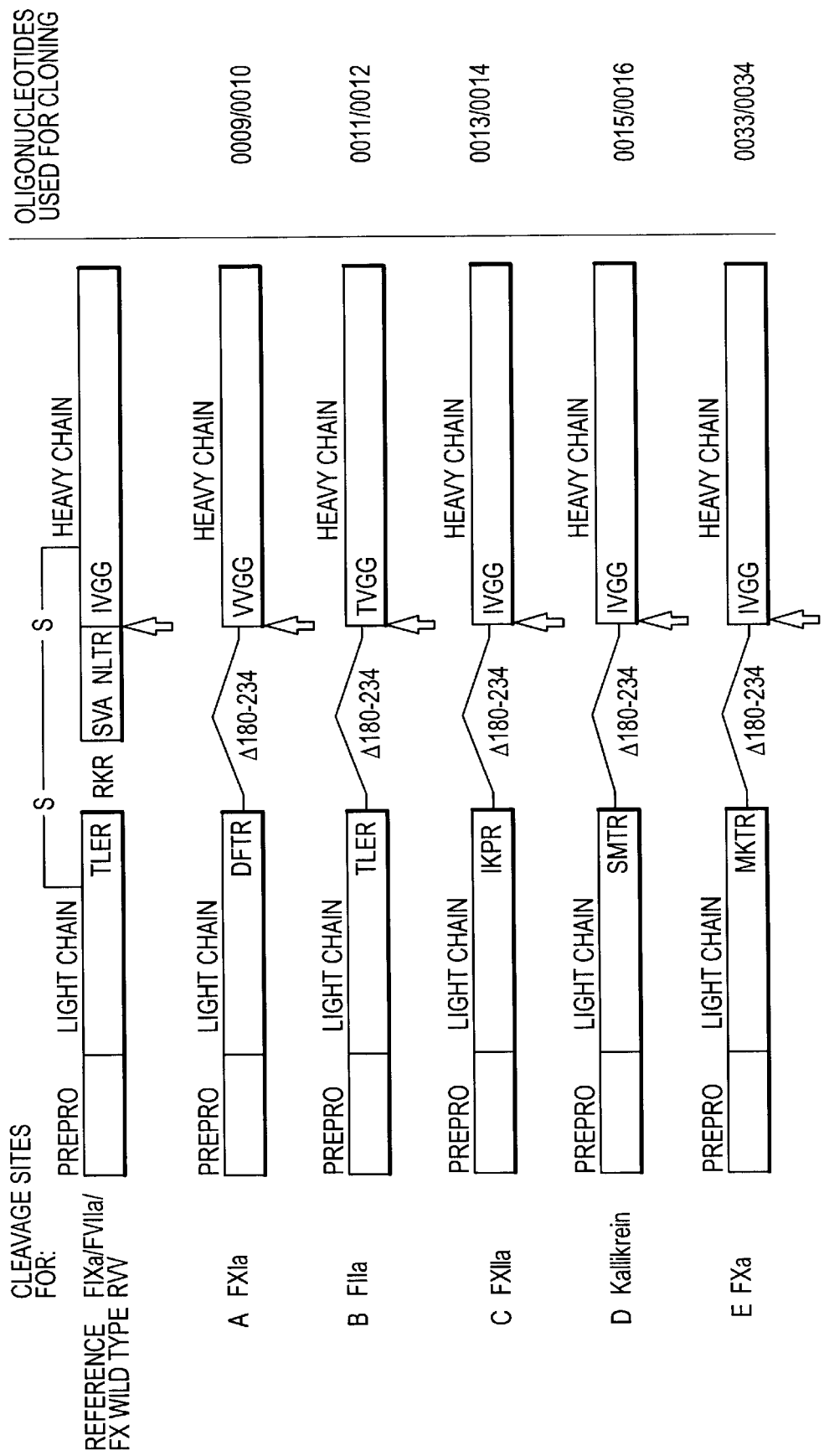
FIGS. 2A and 2B show a schematic representation of the factor XΔ analogues having modified protease cleavage sites (SEQ ID NOS:102–119).
Figure 2B:
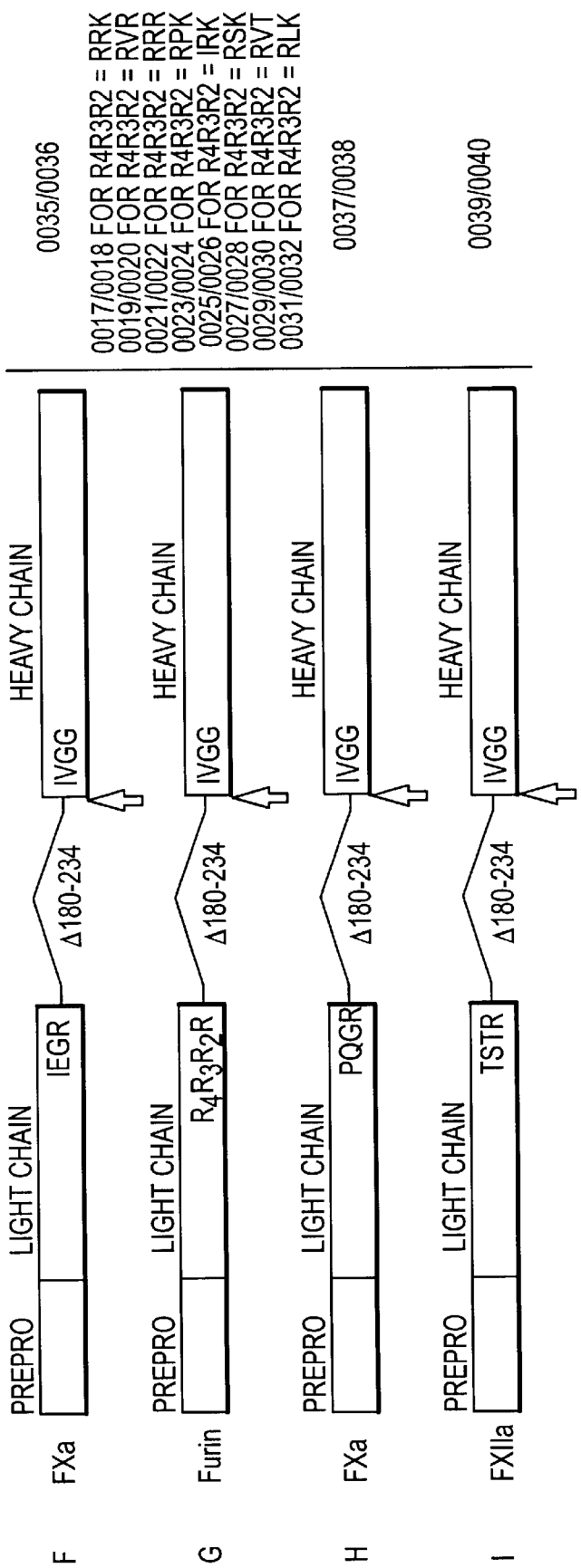

FIGS. 2A and 2B show a possible selection of modifications and amino acid exchanges leading to changed protease specificity.

The modifications can be carried out by, for instance, directed in vitro mutagenesis or PCR or other methods of genetic engineering known from the state of the art which are suitable for specifically changing a DNA sequence for directed exchanges of amino acids.

According to the present invention, the factor XΔ analogue of the invention is preferably activated to a factor Xa analogue by a protease selected from the group of endoproteases, such as kexin/Kex2, furin/PACE, PC1/PC3, PC2, PC4, PACE 4, LPC/PC7, serine proteases, such as factor IIa, factor VIIa, factor IXa, factor XIIa, factor XIa, factor Xa, or kallikrein, or a derivative of these proteases.

The factor XΔ analogues according to the invention are present as single chain polypeptides in enzymatically inactive form. Active factor Xa analogues are only obtained by cleavage by a protease to the double chain form. Thus, the modification allows activation of the inactive, single chain factor XΔ analogue polypeptide to the double chain active form.

One of the difficulties in the preparation of active factor Xa is its instability, because autocatalysis results in the formation of other, inactive intermediates besides factor Xaα and factor Xaβ.

For the preparation of essentially intact, active factor X/Xa and factor X/Xa-like molecules, respectively, it would therefore be desirable to obtain only such proteins as result in stable final products.

It is well known that a preferred cleavage site for the processing of factor Xaα (FXaα) to factor Xaβ (FXaβ) is between Arg469/Gly470. Based on research by Eby et al. (1992, Blood. Vol. 80, Suppl. 1, 1214), next to a prominent carboxy-terminal peptide (amino acid residues 476–487) of factor X, another, shorter peptide (amino acid residues 474–477) is found which is formed by autocatalysis of factor Xaα. In order to focus directed processing of intact factor X to essentially active factor Xa without obtaining inactive processing intermediates, the factor XΔ analogues of the invention optionally have further modifications.

Therefore, according to a particular embodiment, the factor XΔ analogues according to the invention have one further modification in the C-terminal region of the factor X amino acid sequence.

According to one embodiment, a factor XΔ analogue as described above has an intact β-peptide (FXha). The factor XΔ analogues according to the invention particularly have a modification in the region of the C-terminal β-peptide cleavage site which prevents cleavage of the β-peptide from factor X after activation of factor XΔ to factor Xa analogue. Thus a factor Xa molecule is obtained which can be isolated up to 100% as intact factor Xaα molecule.

Said modification can be a mutation, deletion or insertion in the region of the factor X amino acid sequence between amino acid position Arg469 and Ser476 and optionally of Lys370. However, an amino acid substitution is preferred which prevents the polypeptide from folding as a consequence of the amino acid exchange, which would influence the structure and thus possibly the function and activity of the protein.

According to one embodiment, the factor XΔ analogues of the invention have one of the amino acids at position Arg469 and/or Gly470 exchanged, with Arg469 being preferably exchanged for Lys, His or Ile, and Gly470 being preferably exchanged for Ser, Ala, Val or Thr.

Besides a mutation at position Arg469 and/or Gly470, the factor XΔ analogues according to the invention can have a further mutation at position Lys370 and/or Lys475 and/or Ser476. Amino acid substitution at this (these) position(s) prevents processing of factor Xaα analogue to factor Xaβ analogue or C-terminal truncated factor Xa analogues, respectively, because the natural occurring sequence(s) is (are) modified such that an occasional autocatalytic cleavage of a carboxy-terminal peptide becomes impossible.

According to a different embodiment, the factor X analogues of the invention have deleted carboxy terminal β-peptide (FXΔβ). Such a factor X analogue can be prepared by expressing a cDNA coding for factor XΔ analogue in a recombinant expression system, cloning only those sequences that code for the amino acids Met1 to Arg179/Ile235 to Arg469.

According to a further embodiment, the factor XΔ analogues according to the invention have a translation stop signal in the C-terminal region of the factor X sequence. This translation stop signal is preferably located at a position following a C-terminal amino acid formed after natural processing. Therefore, the translation stop signal is preferably at the position of amino acid 470 of the factor X sequence, so that the terminal Arg469 of factor XΔβ is retained. For this purpose, the codon GGC encoding the amino acid Gly470 is substituted by TAA, TAG or TGA.

Another aspect of the present invention relates to factor XΔ analogues which are activated to factor Xa analogues by treatment with an appropriate protease in vitro, i.e. the activated factor XΔ analogues. Depending on the factor XΔ analogue used and activated, a factor XaΔ analogue is obtained which, at the C-terminal end of the light chain, has corresponding amino acid modifications, as compared to the natural factor Xa sequence. According to the invention, these modifications are, however, selected in such a way as not to negatively affect the biological activity.

If such a factor X analogue additionally has a translation stop signal in the C-terminal region of the β-peptide, modified factor Xaβ molecules are obtained. If, however, a factor X analogue is employed which has modification(s) within the β-peptide sequence resulting in the β-peptide not being cleaved off, a factor Xaα analogue with an amino acid exchange in the C-terminus of the molecule is obtained.

The factor XΔ analogues according to the invention only have modifications which change the specificity for the ability to be activated and do not significantly influence the activity. Therefore, in any case, biologically and functionally active factor Xa molecules or factor Xa analogues, respectively, are obtained.

In vitro activation can be effected by a protease selected from the group of endoproteases, such as kexin/Kex2, furin/PACE, PC1/PC3, PC2, PC4, PACE 4, LPC/PC7, serine proteases, such as factor IIa, factor VIIa, factor IXa, factor XIIa, factor XIa, factor Xa, or kallikrein, or a derivative of these proteases. It is within the scope of the present invention to use any protease, except RVV or trypsin, as long as it is apt to process the factor XΔ analogue according to the invention to factor Xa analogue.

Although Wolf et al. (1991, J. Biol. Chem. 266:13726–137309), for instance, have assumed that an endopeptidase, such as Kex2, furin or PACE, is involved in the processing of the factor Xa deletion mutant described by this group, they do not give a hint as to the influence of one of these proteases on the processing of factor X. Similarly, U.S. Pat. No. 5,660,950 describes the recombinant preparation of PACE and the use of the protease to improve processing of vitamin K dependent proteins. In a long list of blood factors, factor X is mentioned among others, but no data are provided to verify this statement.

The present invention demonstrates unambiguously for the first time that a protease necessary for the maturing process of factor X is a dibasic endoprotease, particularly endogenic furin. In vivo, the endoprotease mainly mediates the cleavage of the single chain factor X molecule to the mature form consisting of heavy and light chain. In vitro, it also mediates the cleavage of the factor X propeptide sequence (Example 2).

According to a particular embodiment, a factor XΔ analogue is provided which is preferably present in purified form as a single chain molecule. Factor XΔ analogues having in the modified region a cleavage site for a protease not present in recombinant cells are obtained after expression as single chain molecules. The single chain factor XΔ molecule is particularly characterized by high stability and molecular integrity. So far, a single chain, inactive factor XΔ molecule could not be isolated in purified form, because in recombinant cells it is processed to factor Xa and a number of other, also inactive, intermediates (Wolf et al., 1991, J. Biol. Chem. 266:13726–13730). The isolated single chain factor XΔ analogue can be activated by specific processing directly to the double chain factor Xa analogue form. This can be effected by bringing a single chain factor XΔ molecule isolated from a recombinant cell into contact with a protease cleaving the activation site present in the factor XΔ analogue. If, for example, a factor XΔ analogue having a furin activation site is expressed in a furin deficient cell, it can be isolated as a single chain factor XΔ analogue and processed to an active, double chain factor XΔa analogue by bringing it into contact with a dibasic protease, such as furin/PACE or Kex2. Factor XΔ analogues having a processing site for serine protease or kallikrein can also be isolated as single chain molecules in furin expressing cells and then processed with the serine protease to active factor Xa analogues.

Due to the selective and directed processing reaction, a factor Xa analogue thus obtained has high stability and structural integrity and, in particular, is free of inactive factor X/Xa analogue intermediates and autoproteolytic decomposition products.

According to the present invention, the factor XΔ analogue of the invention is provided in the form of a factor XΔa having intact β-peptide as well as in the form of a factor XΔ analogue having a deletion of the β-peptide.

Another aspect of the present invention relates to recombinant DNA encoding the factor XΔ analogues of the invention. Said recombinant DNA results after expression in a factor XΔ analogue with an amino acid sequence corresponding to human factor X except for a deletion of amino acids from Arg180 to Arg234 and a modification allowing processing and activation to active factor Xa analogues having both intact as well as deleted β-peptide.

A further aspect of the invention relates to a preparation containing a purified factor XΔ analogue having a deletion of amino acids from Arg180 to Arg234 and a modification of amino acids in the region between Gly173 and Arg179 and optionally of Ile235. Said modification leads to a novel recognition or cleavage site not naturally located at this position in the polypeptide for a protease which usually does not process the polypeptide at this position. Said preparation can be a purified preparation containing single chain factor XΔ analogue, the polypeptides being obtained from a cell culture system either after isolation from the cell culture supernatant or from a cell culture extract. A recombinant factor XΔ analogue prepurified from a cell culture system can be further purified by methods known from the prior art. Chromatographic methods are particularly useful for this purpose, such as gel filtration, ion exchange or affinity chromatography.

According to one embodiment, the preparation according to the invention contains the factor XΔ analogue as a single chain molecule in enzymatically inactive form, with the factor XΔ analogue having a purity of at least 80%, preferably at least 90%, particularly preferably at least 95%, and the purified preparations containing no inactive, proteolytic intermediates of factor X/Xa analogues.

According to a particular aspect, the preparation contains single chain factor XΔ analogue having a modification allowing activation to factor Xa analogues by one of the proteases selected from the group of dibasic endoproteases, such as kexin/Kex2, furin/PACE, PC1/PC3, PC2, PC4, PACE 4, LPC/PC7, serine proteases, such as factor IIa, factor VIIa, factor IXa, factor XIIa, factor XIa, factor Xa, or kallikrein, or a derivative of these proteases. The activation is effected by bringing the factor XΔ analogue into contact with the appropriate protease, which cleaves at the modified sequence, whereby a factor Xa analogue is obtained.

In the preparation according to the invention, the factor XΔ analogue can be present either as factor XΔα (FXΔα) having intact β-peptide, or as factor XΔβ having a deletion of the β-peptide or other C-terminal deletions.

According to a further embodiment, the preparation according to the present invention contains the factor XΔ analogue preferably as a single chain molecule in isolated form. For this purpose, factor XΔ analogue is obtained, for instance, by recombinant preparation, as a single chain molecule having one modification allowing activation to factor Xa analogue in vitro. The activation of factor XΔ analogue to factor Xa analogue can be effected by bringing factor X analogue into contact with a protease selected from the group of dibasic endoproteases, such as kexin/Kex2, furin/PACE, PC1/PC3, PC2, PC4, PACE 4, LPC/PC7, serine proteases, such as factor IIa, factor VIIa, factor IXa, factor XIIa, factor XIa, factor Xa, or kallikrein, or a derivative of these proteases. The protease can be immobilized on a carrier.

The preparation according to the invention can serve as a starting material for the production and recovery of factor Xa analogues. For large-scale production, the preparation containing single chain factor XΔ analogue is brought into contact with an optionally immobilized protease under conditions allowing optimal activation of factor XΔ analogue to factor Xa analogue, and factor Xa analogues are obtained. The factor Xa analogue thus recovered can subsequently be purified by generally known methods and formulated to a pharmaceutical composition having factor Xa activity.

According to a further aspect of the present invention, a preparation is provided containing a factor Xa analogue having high stability and structural integrity, which is particularly free of inactive factor X/Xa analogue intermediates and autoproteolytic decomposition products. It is obtainable by activating a factor XΔ analogue of the above-defined type and preparing a corresponding preparation.

According to a particular embodiment, the preparation containing the purified, single chain or double chain factor XΔ analogue contains a physiologically acceptable carrier and is optionally formulated as a pharmaceutical preparation. The formulation can be effected according to a method common per se, and it can be mixed with a buffer containing salts, such as NaCl, $CaCl_2$, and amino acids, such as glycin and/or lysin, at a pH in the range of 6 to 8 and formulated as a pharmaceutical preparation. The purified preparation containing factor X analogue can be provided as a storable product, as a ready-made solution, lyophilisate or deep frozen until final use. Preferably, the preparation is stored in lyophilized form and dissolved with an appropriate reconstitution solution to an optically clear solution.

However, the preparation according to the present invention can also be provided as a liquid preparation or in the form of deep frozen liquid.

The preparation according to the invention is particularly stable, i.e. it can be left standing in dissolved form over an extended period of time before application. It has appeared that the preparation according to the invention suffers no loss in activity for several hours up to days.

The preparation according to the invention can be provided in an appropriate device, preferably an application device, in combination with a protease selected from the group of endoproteases, such as kexin/Kex2, furin/PACE, PC1/PC3, PC2, PC4, PACE 4, LPC/PC7, serine proteases, such as factor IIa, factor VIIa, factor IXa, factor XIIa, factor XIa, factor Xa, or kallikrein, or a derivative of these proteases.

The preparation according to the invention containing a factor XΔ analogue in combination with a protease able to activate the factor XΔ analogue to factor Xa analogue can be provided as a combination preparation consisting of a vessel containing a protease immobilized on a carrier, optionally in the form of a small column or a syringe charged with an immobilized protease, and a vessel containing the pharmaceutical preparation with factor XΔ analogue. For activation of the factor XΔ analogue, the solution containing the factor XΔ analogue is pressed over the immobilized protease, for instance. During storage of the preparation, the solution containing factor XΔ analogue is preferably kept apart from the immobilized protease. The preparation according to the invention can be present in the same vessel as the protease, with the components, however, being separated in space by an impermeable separation wall which can be easily removed to use the product. The solutions can also be stored in individual vessels and brought into contact only shortly before application.

In a particular embodiment, the protease used for activation is a serine protease naturally involved in blood coagulation, such as factor XIIa, which need not be separated from the activated factor Xa analogue before application but can be applied together with it.

Factor XΔ analogue can be activated to factor Xa analogue shortly before direct use, i.e. before application to the patient. The activation can be effected by bringing it into contact with an immobilized protease or by mixing solutions containing a protease on the one hand and factor XΔ analogue on the other. Thus, it is possible to keep the two components in solution separately and to mix them by means of an appropriate device wherein the components get into contact with each other while passing through, and thus to activate factor XΔ analogue to factor Xa analogue. The patient will be administered a mixture of factor Xa and another serine protease which has effected the activation. Particular care has to be taken as regards the dosage, because endogenous factor X is activated by the additional administration of a serine protease, which might result in shorter clotting time.

According to a preferred embodiment, the pharmaceutical preparation is provided in an appropriate device, preferably an application device, either in frozen liquid or in lyophilized form. An appropriate application device can be a double compartment syringe as described in AT 366 916 or AT 382 783.

According to a further aspect of the invention, the preparation according to the invention optionally contains a blood factor in the form of a zymogen or an active serine protease as a further component. Preferred further components are components having FEIB activity. Among them are, in particular, factor II, factor VII, factor IX, factor VIII, factor V and/or the active serine proteases thereof. Further components can also be phospholipids, Ca ions etc. According to a particular embodiment of the invention, the preparation according to the invention contains at least one further component having FEIB activity.

The preparation according to the invention can be provided as a pharmaceutical preparation having factor Xa activity as a single component preparation or in combination with other factors as a multiple component preparation.

Before processing to a pharmaceutical preparation, the purified protein is subjected to the usual quality controls and brought into a therapeutically administrable form. In recombinant preparation, the purified preparation is particularly tested for the absence of cellular and expression vector derived nucleic acids, preferably according to a method as described in EP 0 714 987.

As, in principle, any biological material can be contaminated with infectious germs, the preparation is optionally treated for inactivation or depletion of viruses in order to produce a safe preparation.

A further aspect of the invention refers to the use of a preparation as described above in the preparation of a medicament. A medicament containing a factor XΔ analogue according to the invention and a correspondingly activated factor X analogue is particularly useful in the treatment of patients suffering from blood coagulation disorders such as patients suffering from hemophilia or patients who have developed inhibiting antibodies against the therapeutic agent administered, e.g. against factor VIII or factor IX.

A further aspect of the invention relates to a method for the preparation of the factor XΔ analogue and a preparation containing the factor XΔ analogue according to the invention. The sequence encoding the factor XΔ analogue is inserted into an appropriate expression system, and appropriate cells are transfected with the recombinant DNA. Preferably, permanent cell lines are established which express factor XΔ analogue. The cells are cultivated under optimal conditions for gene expression, and factor X analogues are isolated either from a cell culture extract or from the cell culture supernatant. The recombinant molecule can be further purified by all known chromatographic methods, such as anion or cation exchange, affinity or immunoaffinity chromatography or a combination thereof.

For the preparation of the factor XΔ analogues according to the invention, the entire cDNA encoding the factor X is cloned in an expression vector. This is effected according to generally known cloning techniques. Subsequently, the nucleotide sequence encoding factor X is modified such that the sequences encoding the amino acids Arg180 to Arg234 are deleted and amino acids in the region between Gly173 and Arg179, optionally Ile235, are modified such that a factor XΔ molecule as described above can be produced. This is effected by genetic engineering techniques known from the state of the art, such as directed in vitro mutagenesis, deletion of sequences, e.g. by restriction digestion by endonucleases and insertion of other, changed sequences, or by PCR. The factor XΔ mutants thus prepared are then inserted into an expression system appropriate for recombinant expression and are expressed.

The factor XΔ analogues according to the invention can also be prepared by chemical synthesis.

The factor XΔ analogues are preferably produced by recombinant expression. They can be prepared by means of genetic engineering with any usual expression systems, such as, for instance, permanent cell lines or viral expression systems. Permanent cell lines are prepared by stable integration of the foreign DNA into the host cell chromosome of, e.g., vero, MRC5, CHO, BHK, 293, Sk-Hep1, particularly liver and kidney cells, or by an episomal vector derived, e.g., from the papilloma virus. Viral expression systems, such as, for instance, the vaccinia virus, baculovirus or retroviral systems, can also be employed. As cell lines, vero, MRC5, CHO, BHK, 293, Sk-Hep1, gland, liver and kidney cells are generally used. As eukaryotic expression systems, yeasts, endogenous glands (e.g. glands of transgenic animals) and other types of cells can be used, too. Of course, transgenic animals can also be used for the expression of the polypeptides according to the invention or derivatives thereof. For the expression of the recombinant proteins, CHO-DHFR$^-$ cells have proved particularly useful (Urlaub et al., Proc. Natl. Acad. Sci., U.S.A., 77:4216–4220, 1980).

For the recombinant preparation of factor XΔ analogues according to the present invention, prokaryotic expression systems can be used, too. Systems allowing expression in *E. coli* or *B. subtilis* are particularly useful.

The factor XΔ analogues are expressed in the respective expression systems under control of a suitable promotor. For expression in eukaryotes, all known promoters are suitable, such as SV40, CMV, RSV, HSV, EBV, β-actin, hGH or inducible promoters, such as, for instance, hsp or metallothionein promotor. The factor X analogues are preferably expressed under control of the β-actin promotor in CHO-DHFR$^-$ cells.

According to an embodiment of the invention, the method for preparing the preparation of the invention comprises the steps of: providing a DNA encoding a factor XΔ analogue, transforming a cell with the recombinant DNA, expressing the factor X analogue, optionally in the presence of a protease, isolating the factor X analogue, and optional purifying by means of a chromatographic method.

According to an embodiment of the process, the factor Xa analogue is directly isolated as a double chain molecule. A factor XΔ analogue having a modification allowing processing by a dibasic protease, such as furin, is expressed in a cell, and the factor XΔ analogue is processed to double chain factor Xa analogue. The cell is preferably a cell expressing a protease able to process, e.g. a dibasic protease, such as furin or a derivative thereof. To improve or enhance processing efficiency, the cell can optionally be modified such that its protease expression is enhanced. For instance, this can be effected by co-expression of a corresponding dibasic endoprotease, such as furin/PACE, Kex2 or a derivative thereof. The factor XΔ analogue according to the invention can also be expressed in a cell having normal endogenous protease concentration, i.e. a suboptimal concentration for processing, resulting in incomplete processing into the double chain active form. In this case, as long as single chain factor X analogue is secerned into the cell culture supernatant as described above, subsequent processing into factor Xa analogue is effected by co-cultivation with protease expressing cells or bringing into contact with an optionally immobilized protease. The cell supernatant can also be pumped over a carrier matrix having protease bound thereto, thus yielding double chain factor Xa analogue in the eluate.

The factor Xa analogue thus obtained can subsequently be isolated, purified and optionally formulated as a pharmaceutical composition and stored stably until further use, as described above. The reaction conditions for the processing reaction and activation can be easily optimized by a person skilled in the art according to the experimental setup and the given basic conditions. For the contact time, the flow rate of the present reactants is of particular importance. It should be between 0.01 ml/min and 1 ml/min. Further important parameters are temperature, pH value and eluation conditions. After passage, factor Xa analogue can optionally be further purified by selective chromatography. It is particularly advantageous to conduct the process with protease bound to a carrier, because when using a carrier, preferably chromatographic columns, the reaction setup allows an additional purification step.

According to an embodiment, activation is effected by a chromatographic step, wherein protease is immobilized on a carrier. Purified single chain factor XΔ analogue is conducted over a matrix having protease bound thereto, and purified factor Xa analogue is isolated from the eluate.

According to an aspect of the invention, a preparation containing active factor Xa analogue is obtained by subjecting factor XΔ analogue prepared as described above to a processing/activation step and further processing the activated polypeptide to a purified preparation optionally formulated as a pharmaceutical composition.

According to a further aspect of the production of a preparation containing single chain factor XΔ analogue, e.g., the factor XΔ analogue having a processing sequence for a dibasic protease is expressed in a cell having endoprotease deficiency. The cell is preferably deficient in a dibasic endoprotease, such as kexin, furin, PACE or homologous derivatives thereof. From such an endoprotease deficient mutant cell, factor XΔ analogue can be isolated as a single chain molecule. Factor XΔ analogues having a processing site for a serine protease can be expressed in any conventional cell, including furin positive cells, and isolated as a single chain molecule.

A factor X analogue thus isolated and optionally purified is subsequently brought into contact with a protease selected from the group of endoproteases, such as kexin/Kex2, furin/PACE, PC1/PC3, PC2, PC4, PACE 4, LPC/PC7, serine proteases, such as factor IIa, factor VIIa, factor IXa, factor XIIa, factor XIa, factor Xa, or kallikrein, or a derivative of these proteases, under conditions under which a single chain factor X analogue is cleaved and activated to factor Xa analogue.

With the factor XΔ analogues according to the invention which are activated by a process as described above to factor Xa analogues, a purified factor Xa analogue having high stability and structural integrity and being particularly free of inactive factor X/Xa intermediates is obtained.

The invention is described in more detail by the following Examples and drawing figures, with the invention, however, not being restricted to these particular examplary embodiments.

Example 1 describes the construction and expression of rfactor X; Example 2 describes the processing of rfactor X into heavy and light chain by furin; Example 3 describes the processing of pro-factor X by means of immobilized protease; Example 4 describes the activity of rfactor X processed in vitro; Example 5 describes the expression of rfactor X in furin deficient cells; Example 6 describes the construction and expression of rfactor XΔ analogues; Example 7 describes the determination of N-termini of the factor X processing products; Example 8 describes the expression and characterization of the FX deletion mutant having the site Arg-Val-Thr-Arg/Ile (SEQ ID NO:101) (rFXΔ$^{RVTR/I}$); Example 9 describes in vitro activation of the protein rFXΔ$^{RVTR/I}$ by r-fufin derivatives.

The expression vectors were prepared by means of standard cloning techniques (Maniatis et al., "Molecular Cloning"—A Laboratory Manual, Cold Spring Harbor Laboratory, Cold Spring Harbor, N.Y., U.S.A., 1983). The preparation of DNA fragments by means of polymerase chain reaction (PCR) followed general methods (Clackson et al., 1991, PCR A practical approach. Ed. McPherson, Quirke, Taylor, p. 187–214).

EXAMPLE 1

Figure 3:
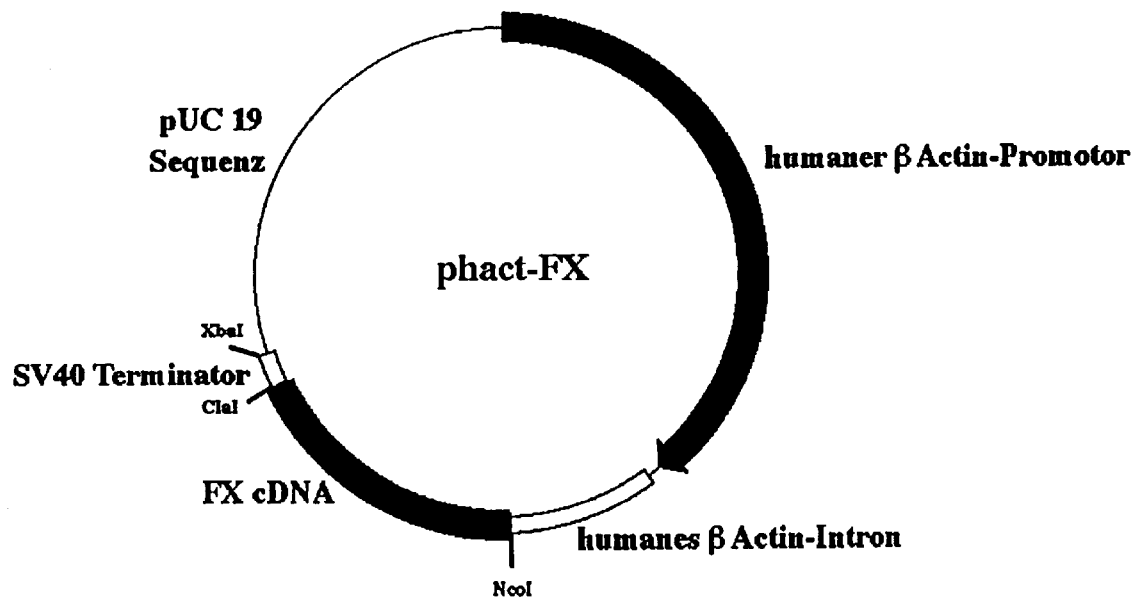
FIG. 3 shows a schematic representation of the expression vector phAct-rFX.

Expression and Processing of Single Chain rFX to rFX Light/Heavy Chain a. Preparation of the rFX Expression Vector For the preparation of recombinant FX (rFX), the cDNA of FX was isolated from a human liver lambda-cDNA-library as described by Messier et al. (1991, Gene 99:291–294). A DNA fragment was amplified from a positive clone by means of PCR with oligonucleotide #2911 (5'-ATTACTCGAGAAGCTTACCATGGGGCGCCCACTG-3') (SEQ. ID No.1) as 5'-primer and oligonucleotide #2912 (5'-ATTACAATTGCTGCAGGGATCCAC-3') (SEQ. ID. No. 2) as 3'-primer, which DNA fragment contains the 1,467 kB FX coding sequence and 39 bp of the 3'-non-translated region, flanked by a XhoI cleavage site at the 5'-end and a MfeI cleavage site at the 3'-end. In addition, the sequence ACC was incorporated in front of the ATG of the FX by means of primer #2911 resulting in an optimal Kozak translation initiation sequence. Subsequently, this PCR product was cloned as XhoI/MfeI fragment in the expression vector phact cleaved with SalI and EcoRI. The resulting expression plasmid was designated as phAct-rFX (FIG. 3). The expression vector phAct comprises the human beta-actin-promotor, 78 bp 5'UTR and the intron, a multiple cloning cleavage site, and the SV40 polyadenylation site.

b. Expression of rFX in CHO Cells

Figure 4:
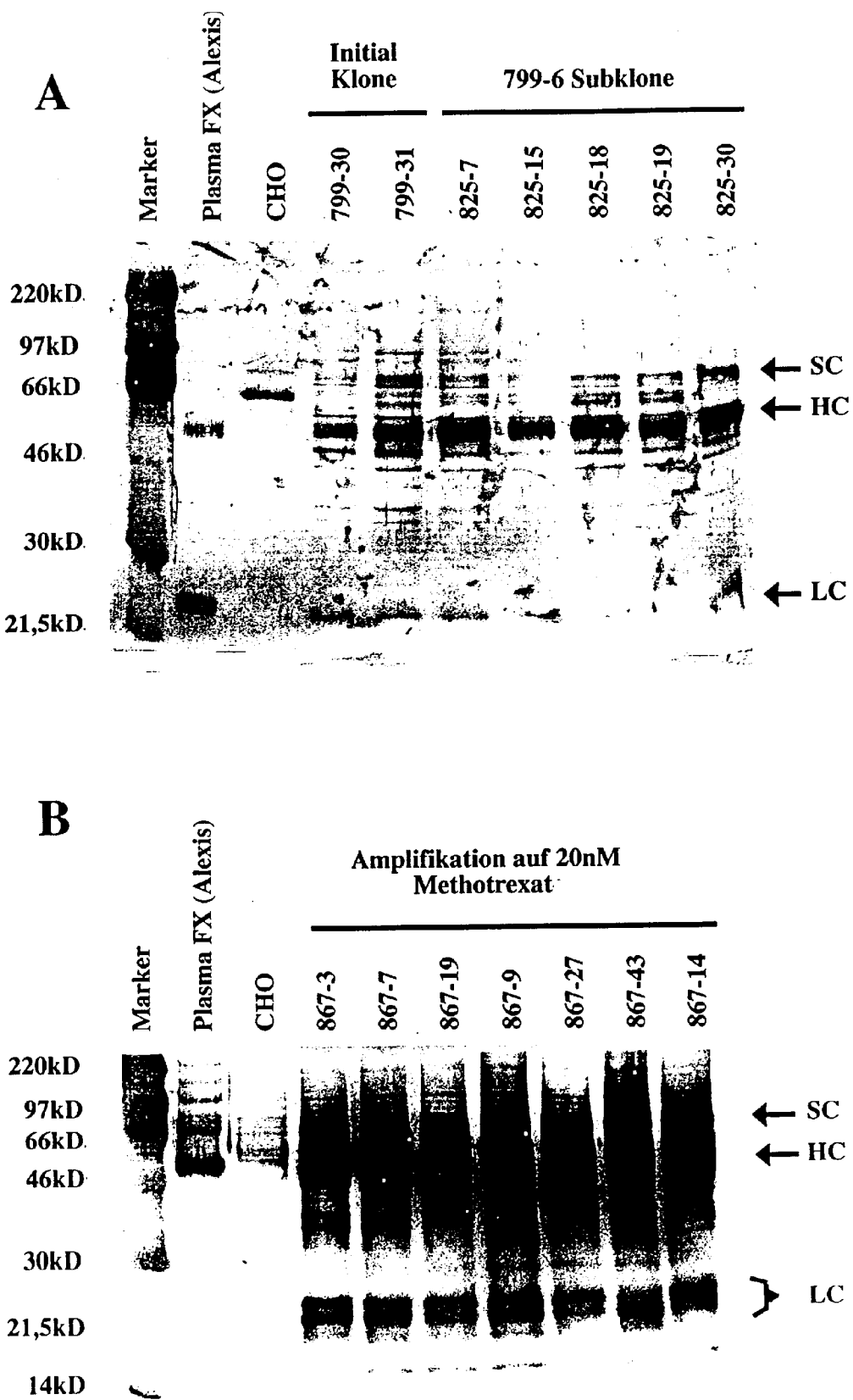
FIGS. 4A and 4B show a Western blot analysis of rfactor X expressed in CHO cells before and after amplification.

In order to establish a stable rFX expressing cell line, dhfr deficient CHO cells were co-transfected with the expression plasmid phAct-rFX and the selection marker plasmid pSV-dhfr. For all further expression and function analyses, the cell cultures were incubated with serum free selection medium in the presence of 10 $\mu$g/ml vitamin K for 24 hours. The expression of rFX in the resulting cell clones was detected by means of the amount of antigen (ELISA, Asserachrom, Boehringer Mannheim), and then the recombinant protein was characterized with SDS-PAGE (FIGS. 4A and B). As can be seen in the Western blot (FIG. 4A), in the initial clones and subclones thereof the recombinant FX protein is present in the form of a light chain (LC) of 22 kD and a heavy chain (HC) of approximately 50 kD, which are identical with the plasmatic factor X protein. In addition, a protein band is visible at 75 kD, which corresponds to the single chain (SC) molecule and the presence of which in FX transfected CHO cells (Wolf et al., J. Biol. Chem. 266:13726–13730, 1991) and in human plasma (Fair et al., Blood 64:194–204, 1984) has been described. For the preparation of highly expressing clones, the initial clones were amplified with increasing amounts of methotrexate and subsequently subcloned to stabilization. Expression could be increased from about 200–500 ng/10 E6 cells or 1 $\mu$g/ml, respectively, to 78 $\mu$g/10 E6 cells or 120 $\mu$g/ml, respectively, per 24 hours. Western blot analysis of these highly expressing cell clone supernatants (FIGS. 4B and 5A, lane 2) shows enrichment of the single chain rFX molecule and the presence of additional forms of the light chain. Besides the 22 kD form of the light chain, which corresponds to the plasmatic form (completely carboxylated and without propeptide) there are three further light chain variants of about 21 kD, 22.5 kD, and 20 kD present. By means of N-terminal sequencing of the recombinant material, the heterogeneity of the light chain in these clones was determined as a result of incomplete cleavage of the propeptide (here: about 50% of the rFX material) and hypocarboxylation (here: about 50% of the rFX). The 21 kD protein is a hypocarboxylated, propeptide containing form, and the 20 kD protein is a hypocarboxylated, propeptide-free form of the light chain, while the 22.5 kD band represents the fully carboxylated, but propeptide containing LC form.

EXAMPLE 2

Processing of Single Chain rFX in rFX Light/Heavy Chain by r-Furin Derivatives

Due to the similarity of the cleavage sites of factor X propeptide/N-terminus of the light chain (RVTR↓A; SEQ ID NO:129) and of light/heavy chain (RRKR↓S; SEQ ID NO:130) to the furin consensus detection sequence (RXK/RR↓X; SEQ ID NO:131), it was possible to improve in vitro processing of single chain as well as propeptide containing rFX molecules by r-furin derivatives. In the literature, proteases are suspected for the two processing steps, which, however, are not furin (Rehemtulla et al., 1992, Blood 79:2349–2355; Wallin et al., 1994, Thromb. Res. 1994:395–403).

Figure 5A:
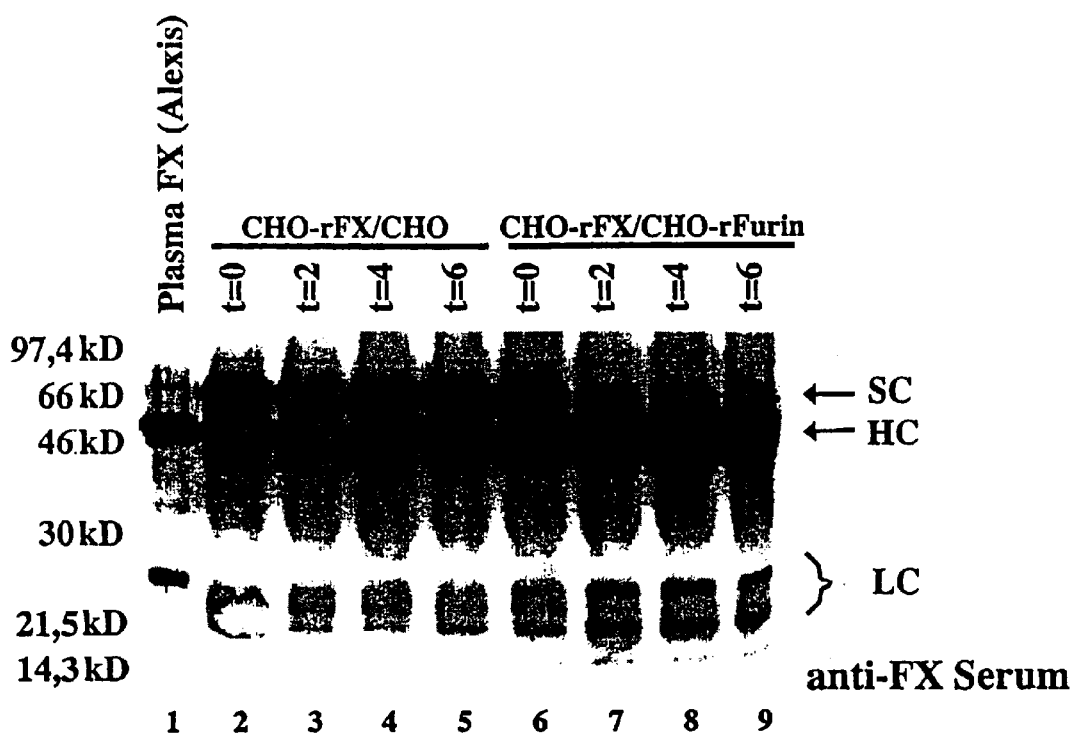
FIGS. 5A and 5B show a Western blot analysis of rfactor X after in vitro cleavage by furin derivatives.
Figure 5B:
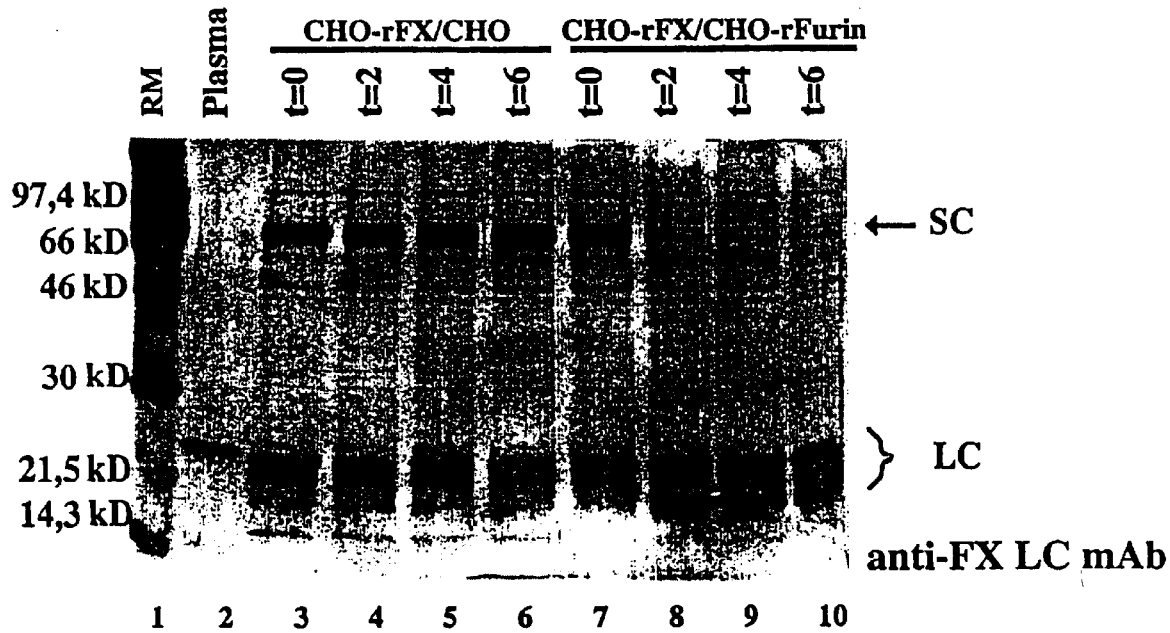

Cell culture supernatants of CHO-rFX and CHO-rfurin ΔTM6xHis (patent application EP 0 775 750) as well as CHO-rFX and non-transfected CHO (as negative control) were mixed at a ratio of 1:1 and incubated at 37° C. Aliquots of the reaction mixtures were tested for processed rFX before incubation (t=0) and after various incubation periods (t=2, 4, 6, hours) by means of Western blot analysis (FIGS. 5A and 5B). The rFX was detected in the cell culture supernatants by means of an anti-human FX antiserum (FIG. 5A) and a monoclonal antibody specific for the light chain of FX (FIG. 5B).

Contrary to the CHO-rFX/CHO mixture, CHO-rFX/CHO-rfurin shows almost complete processing already after 2 hours of incubation at 37° C. (FIG. 5A, lane 7; FIG. 5B, lane 8). Single chain rFX is largely reacted to the light and heavy chain forms. In the area of the light chain, only the processed propeptide-free forms of 22 kD (carboxylated form) and 20 kD (hypocarboxylated form) were found at a ratio of about 50:50. By optimizing cell culture conditions, this ratio can be improved in favor of the carboxylated form. Correct cleavage of the pro-sequence between Arg-1 and Ala+1 and homogeneity of the N-terminus of the light chain were determined by means of N-terminal sequencing. In the control experiment, wherein CHO-rFX was mixed with CHO-supernatants, no change in the rFX band pattern is visible even after 6 hours of incubation (FIG. 5A, lane 5; FIG. 5B, lane 6). This proves that r-furin in the supernatant of CHO cells is biologically active and can process the propeptide as well as the heavy/light chain of rFX.

EXAMPLE 3

Processing of Factor X by Means of Chelate-tentacle Gel Immobilized r-Furin

To determine whether a substrate can be cleaved by a column-bound r-furin derivative, a study was conducted as to whether in an experimental setup Fractogel EMD® tentacle gel (Merck) can be used instead of $Ni^{2+}$-NTA agarose as column matrix. As the metal ions are farther apart from the actual column matrix than the $Ni^{2+}$-NTA agarose, an improved sterical access to the bound r-furin derivative might be achieved. In the present setup, pro-factor X was processed by tentacle gel bound r-furin derivative:

Fractogel EMD® tentacle gel was loaded with $Ni^{2+}$ ions according to the producer's instructions and equilibrated with fresh serum-free cell culture medium. Subsequently, the column was loaded with serum-free CHO-r-furin derivative supernatant. Washing steps were carried out with serum-free cell culture medium containing increasing imidazole concentrations up to 40 mM. Then pro-factor X was passed over the column as serum-free CHO supernatant. Processing of pro-factor X to double chain factor X was detected in the effluent of the column by means of Western blot analysis with specific factor X antiserum.

EXAMPLE 4

Activity of Recombinant Factor X Processed In Vitro

Recombinant factor X precursor was incubated with and without r-furin at 4° C. At different times, samples were taken and frozen at −20° C. After the incubation was completed (after 4 days), all samples were tested for FX activity using a FX Coatest Kit (Chromogenix). 50 µl of each supernatant were mixed with 50 µl FX deficient human plasma, and rFX was reacted with snake venom (RVV) to rFXa in the presence of $CaCl_2$ according to the producer's instructions. rFXa then hydrolyzes the chromogenic substrate (S-2337) and leads to the release of yellow-coloured paranitroaniline. As the amount of rFXa and the intensity of the colour are proportionate to each other, the amount of rFX/ml cell culture supernatant which can be activated to rFXa can be determined by means of a calibration line interpolated from values of a plasma dilution series. Using these results and the known amount of rFX antigen (ELISA data), the proportion of rfactor X activated to factor Xa can be calculated in %. The results are presented in table 1.

In order to exclude nonspecific, proteolytic activity in CHO and CHO-r-furin supernatants, the mixture of these two cell culture supernatants was tested, too.

Even after 4 days, CHO-rFX incubated with CHO supernatants (without r-furin) as control displayed no substantial change in rFXa activity, which was about 800 mU/ml and corresponded to 50% to 60% of functional rFX due to experimental variations. When, in comparison, CHO-rFX was incubated with CHO-r-furin, rFX activity increased steadily during incubation, rising from about 60% (T=0) to 86% (table 1). This proves that in vitro processing of CHO-rFX from highly expressing clones using r-furin derivative substantially improves the proportion of rFX that can be activated to functional rFXa.

TABLE 1

| | incubation (days) | activity (mU) | amount of antigen (µg/ml) | functional portion of rFX (%) |
|---|---|---|---|---|
| CHO-rFX + CHO | 0 | 814 | 14 | 58 |
| | 1 | 847 | 14 | 61 |
| | 2 | 835 | 14 | 60 |
| | 3 | 790 | 14 | 56 |
| | 4 | 763 | 14 | 55 |
| CHO-rFX + CHO-rFurin | 0 | 853 | 14 | 61 |
| | 1 | 1018 | 14 | 73 |
| | 2 | 1099 | 14 | 79 |
| | 3 | 1135 | 14 | 81 |
| | 4 | 1198 | 14 | 86 |
| CHO + CHO-rFurin | | 0 | | |
| Plasma FX 500 mU | | 585 | | |

EXAMPLE 5

Expression of Recombinant Factor X in Furin Deficient Cells

As shown in the previous Examples, in the case of factor X precursor protein, furin mediates propeptide cleavage as well as cleavage of the single chain to light/heavy chain in vitro. This suggests that these steps are also effected endogenously in the cell by ubiquitous furin with varying efficiency depending on the amount of expressed rfactor X. This in turn leads to the production of a mixture of heterogenous rfactor X forms.

One way to prepare a form of rfactor X molecules which is as homogeneous as possible and also stable is to prevent cleavage of rfactor X by endogenous proteases, particularly furin, and thus to produce functionally inactive rfactor X precursors (which can be transformed into its functionally active form later by means of downstream processing, ideally directly before use). This process will be particularly useful in the preparation of FX deletion mutants containing a furin cleavage site instead of the original activation site. In these constructs, such a recombinant rFX mutant in vivo can be activated by endogenous furin and lead to the secretion of activated, more instable rFX forms. Degradation of these forms by CHO proteases, e.g. under cell culture conditions of high cell lysis, during storage of the cell culture supernatants or the purifying process could result in inactive degradation products (Wolf et al., 1991).

This aim can, for instance, be achieved by supplementing the cell culture medium with agents which can reduce or prevent intracellular furin activity.

Another way is to use cells which are furin deficient a priori (Möhring et al., 1983, Infect. Immun. 41:998–1009; Ohnishi et al., 1994, J. Virol. 68:4075–4079; Gordon et al., 1995, Infect. Immun. 63:82–87).

Figure 6:
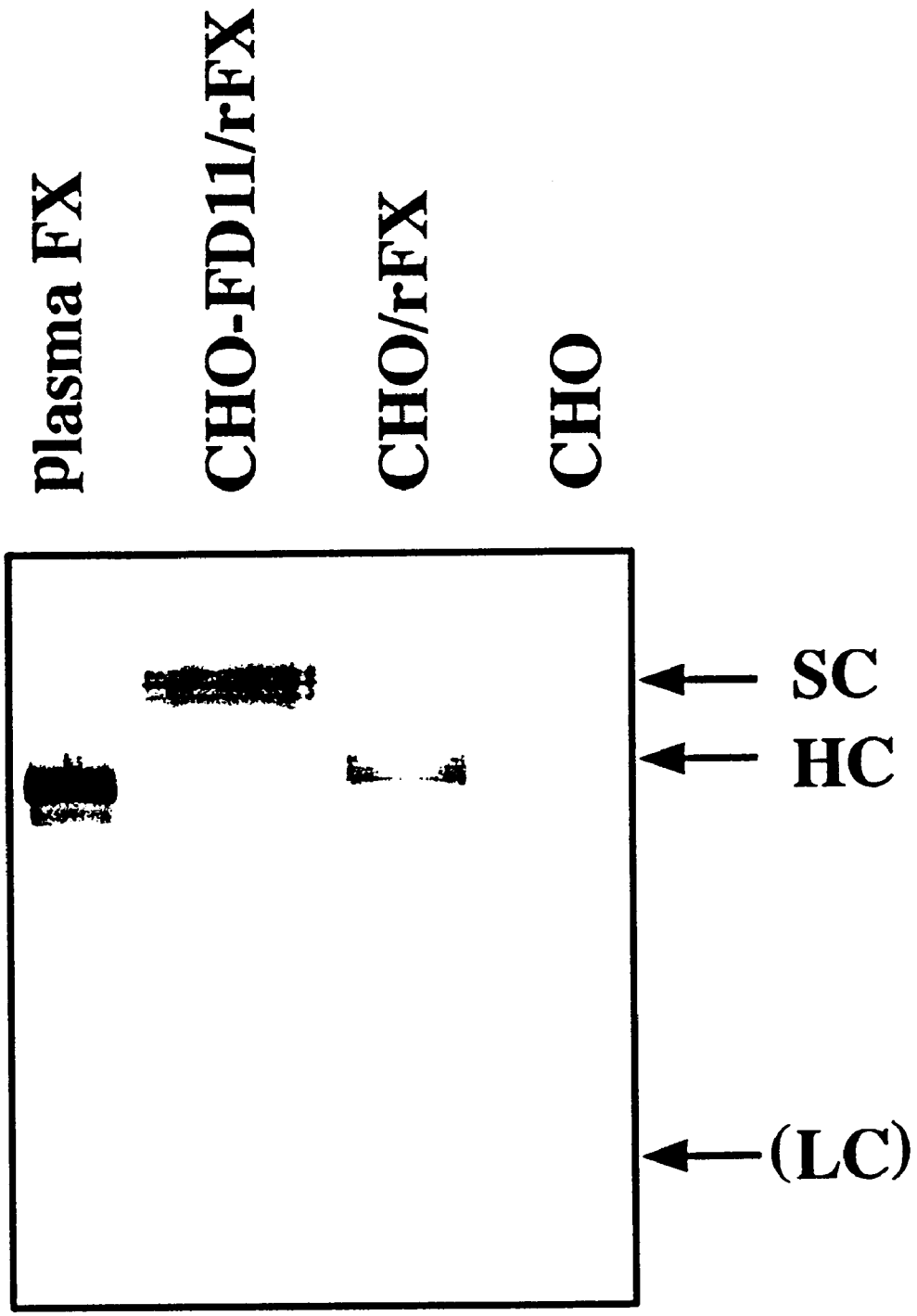
FIG. 6 shows a Western blot analysis of rfactor X molecules expressed in furin containing and furin deficient cells.

For this purpose, a furin deficient CHO cell clone FD11 (Gordon et al., 1995, Infect. Immun. 63:82–87) was co-transfected with 20 µg phAct-FX and 1 µg pUCSV-neo (containing the neomycin resistance gene in the pUC vector under control of the SV40 promotor). In order to obtain stable clones, the medium was supplemented with 0,8 µg G418/ml. Comparing secerned rfactor X molecules in serum free supernatants of a furin containing and a furin deficient CHO clone, Western blot shows that rfactor X precursor is not processed in the furin deficient cells and only single chain factor X precursor is present (FIG. 6); in contrast, rfactor X is still completely processed by "normal" cells with modest expression, but is processed only to a very limited extent with higher expression in spite of endogenous furin. Due to the low degree of rFX expression of the cell clone used, the light chain of rfactor X here is not visible in the blot.

EXAMPLE 6

Preparation of Factor XΔ Analogues (at Present, the Applicant Regards this as the Best Mode for Carrying Out the Invention)

6.1. Construction of Expression Plasmids for the Preparation of FX Deletion Mutants Factor X deletion mutants differ from the factor X wild type sequence in the deletion of the app. 4.5 kDa activation peptides between amino acid 180 and 234. In addition, various cleavage sites were introduced into the C-terminus of the light chain and/or the N-terminus of the heavy chain by means of mutagenesis, which sites function to activate the single chain factor X molecule resulting therefrom to the activated polypeptide. Expression plasmids for these factor X deletion mutants are all derived from phAct-FX (described in Example 1).

In order to simplify the cloning of factor X deletion mutants, the HindIII-NaeI DNA fragment from plasmid phAct-FX, which comprises the factor X encoding region from position +1 to +1116, was inserted into the HindIII/SmaI restriction cleavage sites of plasmid pUC19. The resulting plasmid was designated as pUC/FX. In order to delete the activation peptide and to incorporate new cleavage sites, e.g. furin, FXIa, FXIIa, FXa, FIIa cleavage sites, the Bsp120I/BstXI FX DNA fragment from the pUC/FX vector was replaced by synthetic oligonucleotides. In order to incorporate a thrombin or FXIa cleavage site, the BstXI-3'-overlap was smoothened by mung bean nuclease, so that amino acid Ile at position 235 could be exchanged, too. Subsequently, the deleted factor X DNA fragments were cloned in plasmid pACT-FX via HindIII-AgeI.

In order to prepare the Asp-Phe-Thr-Arg/Val (SEQ ID NO:132) FXIa cleavage site, the oligonucleotide sense #0009 (5'-GG CCC TAC CCC TGT GGG AAA CAG GAC TTC ACC AGG GTG-3') (SEQ ID NO:3) and the oligonucleotide antisense #0010 (5'-CAC CCT GGT GAA GTC CTG TTT CCC ACA GGG GTA G-3') (SEQ ID NO:4) were used and inserted into the Bsp120I and the mung bean nuclease treated BstXI sites. Thus, the amino acids from position 176 to 178 and 235 were mutated into Asp-Phe-Thr and Val (FIG. 2A, panel A).

In order to prepare the Arg/Thr FIIa cleavage site, the oligonucleotide sense #0011 (5'-GG CCC TAC CCC TGT GGG AAA CAG ACC CTG GAA CGG ACC-3') (SEQ ID NO:5) and the oligonucleotide antisense #0012 (5'-GGT CCG TTC CAG GGT CTG TTT CCC ACA GGG GTA G-3') (SEQ ID NO:6) were used and inserted into the Bsp120I and the mung bean nuclease treated BstXI sites. Thus, the amino acid lie at position 235 was mutated into Thr (FIG. 2A, panel B).

In order to prepare the Ile-Lys-Pro-Arg/Ile (SEQ ID NO:133) FXIIa cleavage site, the oligonucleotide sense #0013 (5'-GG CCC TAC CCC TGT GGG AAA CAG ATC AAG CCC AGG ATC-3') (SEQ ID NO:7) and the oligonucleotide antisense #0014 (5'-CT GGG CTT GAT CTG TTT CCC ACA GGG GTA G-3') (SEQ ID NO:8) were used and inserted into the Bsp120I and BstXI sites. Thus, the amino acids of position 176 to 178 were mutated into Ile-Lys-Pro (FIG. 2A, panel C).

In order to prepare the Ser-Met-Thr-Arg/Ile (SEQ ID NO:134) kallikrein cleavage site, the oligonucleotide sense #0015 (5'-GG CCC TAC CCC TGT GGG AAA CAG AGC ATG ACC AGG ATC-3') (SEQ ID NO:9) and the oligonucleotide #0016 (5'-CT GGT CAT GCT CTG TTT CCC ACA GGG GTA G-3') (SEQ ID NO:10) were used and inserted into the Bsp120I and BstXI sites. Thus, the amino acids of position 176 to 178 were mutated into Ser-Met-Thr (FIG. 2A, panel D).

In order to prepare the Met-Lys-Thr-Arg/Ile (SEQ ID NO:135) FXa cleavage site, the oligonucleotide sense #0033 (5'-GG CCC TAC CCC TGT GGG AAA CAG ATG AAA ACG AGG ATC-3') (SEQ ID NO:11) and the oligonucleotide antisense #0034 (5'-CT CGT TTT CAT CTG TTT CCC ACA GGG GTA G-3') (SEQ ID NO:12) were used and inserted into the Bsp120I and BstXI sites. Thus, the amino acids of position 176 to 178 were mutated from Thr-Leu-Glu into Met-Lys-Thr (FIG. 2A, panel E).

In order to prepare the Ile-Glu-Gly-Arg/Ile (SEQ ID NO:136) FXa cleavage site, the oligonucleotide sense #0035 (5'-GG CCC TAC CCC TGT GGG AAA CAG ATC GAG GGA AGG ATC-3') (SEQ ID NO:13) and the oligonucleotide antisense #0036 (5'-CT TCC CTC GAT CTG TTT CCC ACA GGG GTA G-3') (SEQ ID NO:14) were used and inserted into the Bsp120I and BstXI sites. Thus, the amino acids in position 176 to 178 were mutated from Thr-Leu-Glu into Ile-Glu-Gly (FIG. 2A, panel F).

In order to prepare the Arg-Arg-Lys-Arg/Ile (SEQ ID NO:137) furin cleavage site, the oligonucleotide sense #0017 (5'-GG CCC TAC CCC TGT GGG AAA CAG AGG AGG AAG AGG ATC-3') (SEQ ID NO:15) and the oligonucleotide antisense #0018 (5'-CT CTT CCT CCT CTG TTT CCC ACA GGG GTA G-3') (SEQ ID NO:16) were used and inserted into the Bsp120I and BstXI sites. Thus, the amino acids in positions 176 to 178 were mutated into Arg-Arg-Lys (FIG. 2A, panel G).

In order to prepare the Arg-Val-Arg-Arg/Ile (SEQ ID NO:138) furin cleavage site, the oligonucleotide sense #0019 (5'-GG CCC TAC CCC TGT GGG AAA CAG AGG GTG AAG AGG ATC-3') (SEQ ID NO:17) and the oligonucleotide antisense #0020 (5'-CT CCT CAC CCT CTG TTT CCC ACA GGG GTA G-3') (SEQ ID NO:18) were used and inserted into the Bsp120I and BstXI sites. Thus, the amino acids of positions 176 to 178 were mutated into Arg-Val-Arg (FIG. 2A, panel G).

In order to prepare the Arg-Arg-Arg-Arg/Ile (SEQ ID NO:139) furin cleavage site, the oligonucleotide sense #0021 (5'-GG CCC TAC CCC TGT GGG AAA CAG AGG AGG AGG AGG ATC-3') (SEQ ID NO:19) and the oligonucleotide antisense #0022 (5'-CT CCT CCT CCT CTG TTT CCC ACA GGG GTA G-3') (SEQ ID NO:20) were used and inserted into the Bsp120I and BstXI sites. Thus, the amino acids of positions 176 to 178 were mutated into Arg-Arg-Arg (FIG. 2A, panel G).

In order to prepare the Arg-Pro-Lys-Arg/Ile (SEQ ID NO:140) furin cleavage site, the oligonucleotide sense #0023 (5'-GG CCC TAC CCC TGT GGG AAA CAG AGG CCC AAG AGG ATC-3') (SEQ ID NO:21) and the oligonucleotide antisense #0024 (5'-CT CTT GGG CCT CTG TTT CCC ACA GGG GTA G-3') (SEQ ID NO:22) were used and inserted into the Bsp120I and BstXI sites. Thus, the amino acids of positions 176 to 178 were mutated into Arg-Pro-Lys (FIG. 2A, panel G).

In order to prepare the Ile-Arg-Lys-Arg/Ile (SEQ ID NO:141) furin cleavage site, the oligonucleotide sense #0025 (5'-GG CCC TAC CCC TGT GGG AAA CAG ATC AGG A AG AGG ATC-3') (SEQ ID NO:23) and the oligonucleotide antisense #0026 (5'-CT CTT CCT GAT CTG TTT CCC ACA GGG GTA G-3') (SEQ ID NO:24) were used and inserted into the Bsp120I and BstXI sites. Thus, the amino acids of positions 176 to 178 were mutated into Ile-Arg-Lys (FIG. 2A, panel G).

In order to prepare the Arg-Ser-Lys-Arg/Ile (SEQ ID NO:142) furin cleavage site, the oligonucleotide sense #0027 (5'-GG CCC TAC CCC TGT GGG AAA CAG AGG AGC AAG AGG ATC-3') (SEQ ID NO:25) and the oligonucleotide antisense #0028 (5'-CT CTT GCT CCT CTG TTT CCC ACA GGG GTA G-3') (SEQ ID NO:26) were used and inserted into the Bsp120I and BstXI sites. Thus, the amino acids of positions 176 to 178 were mutated into Arg-Ser-Lys (FIG. 2A, panel G).

In order to prepare the Arg-Val-Thr-Arg/Ile (SEQ ID NO:101) furin cleavage site, the oligonucleotide sense #0029 (5'-GG CCC TAC CCC TGT GGG AAA CAG AGG GTC ACG AGG ATC-3') (SEQ ID NO:27) and the oligonucleotide antisense #0030 (5'-CT CGT GAC CCT CTG TTT CCC ACA GGG GTA G-3') (SEQ ID NO:28) were used and inserted into the Bsp120I and BstXI sites. Thus, the amino acids of positions 176 to 178 were mutated into Arg-Val-Thr (FIG. 2A, panel G).

In order to prepare the Arg-Leu-Lys-Arg/Ile (SEQ ID NO:143) furin cleavage site, the oligonucleotide sense #0031 (5'-GG CCC TAC CCC TGT GGG AAA CAG AGG CTG AAA AGG ATC-3') (SEQ ID NO:29) and the oligonucleotide antisense #0032 (5'-CT TTT CAG CCT CTG TTT CCC ACA GGG GTA G-3') (SEQ ID NO:30) were used and inserted into the Bsp120I and BstXI sites. Thus, the amino acids of positions 176 and 178 were mutated into Arg and Lys (FIG. 2A, panel G).

In order to prepare the Pro-Gln-Gly-Arg/Ile (SEQ ID NO:144) FXa cleavage site, the oligonucleotide sense #0037 (5'-GG CCC TAC CCC TGT GGG AAA CAG CCC CAA GGA AGG ATC-3') (SEQ ID NO:31) and the oligonucleotide antisense #0038 (5'-CT TCC TTG GGG CTG TTT CCC ACA GGG GTA G-3') (SEQ ID NO:32) were used and inserted into the Bsp120I and BstXI sites. Thus, the amino acids in positions 176 to 178 were mutated from Thr-Leu-Glu into Pro-Gln-Gly (FIG. 2A, panel H).

In order to prepare the Thr-Ser-Thr-Arg/Ile (SEQ ID NO:145) FXIIa cleavage site, the oligonucleotide sense #0039 (5'-GG CCC TAC CCC TGT GGG AAA CAG ACG AGC ACG AGG ATC-3') (SEQ ID NO:33) and the oligonucleotide antisense #0040 (5'-CT CGT GCT CGT CTG TTT CCC ACA GGG GTA G-3') (SEQ ID NO:34) were used and inserted into the Bsp120I and BstXI sites. Thus, the amino acids in positions 177 and 178 were mutated into Ser-Thr (FIG. 2A, panel 1).

In order to prepare an Arg/Ile trypsin cleavage site, the oligonucleotide #0041 (5'-GG CCC TAC CCC TGT GGG AAA CAG ACC CTG GAA CGG ATC-3') (SEQ ID NO:35) and the oligonucleotide antisense #0042 (5'-CG TTC CAG GGT CTG TTT CCC ACA GGG GTA G-3') (SEQ ID NO:36) were used and inserted into the Bsp120I and BstXI sites (FIG. 2A, panel J).

The resulting expression plasmids (see FIG. 3) comprise the human beta-actin-promotor, 78 bp of 5'UTR, the beta-actin-intron, the modified factor X sequence, and 39 bp of the 3'UTR and the SV40 polyadenylation site.

6.2. Construction of Expression Plasmids for the Preparation of FXβ Analogue

Figure 7:
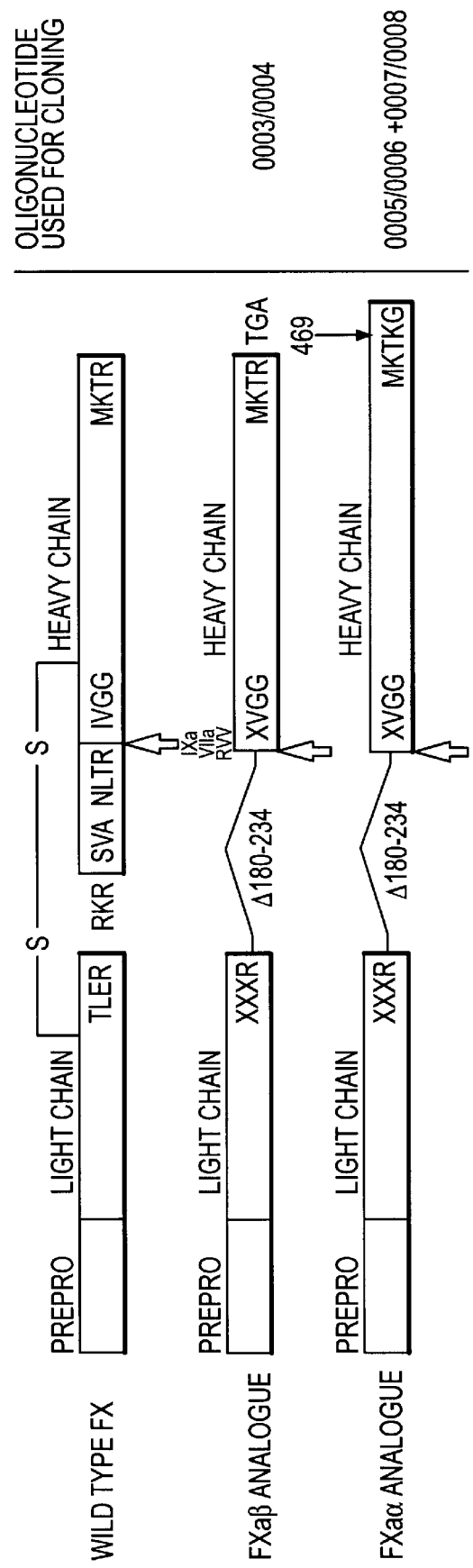
FIG. 7 shows a schematic representation of rfactor XΔ analogue constructs having modified C-termini of the heavy chain (SEQ ID NOS:102, 103 and 120–122).

These constructs were derived from the factor XΔ analogue constructs described above by introducing a TGA stop codon into position 470. The amino acids from position 457 to the stop codon were removed by SpeI and partial BstEII digestion and replaced by the oligonucleotide pair #0003 (5' GTC ACC GCC TTC CTC AAG TGG ATC GAC AGG TCC ATG AAA ACC AGG TGA A-3') (SEQ ID NO:37) and #0004 (5'-CTA GTT CAC CTG GTT TTC ATG GAC CTG TCG ATC CAC TTG AGG AAG GCG-3') (SEQ ID NO:38). FIG. 7 is a schematic representation of the factor XΔβ analogue constructs. In order to simply the figure, all factor XΔβ analogues are represented as a general construct wherein the variable amino acids in the cleavage site region are designated as a shaded "X".

6.3. Construction of Expression Plasmids for the Production of FXΔα Analogue

By activating factor X by cleaving off the 4.5 kDa activation peptide at the N-terminal end of the heavy chain, the factor Xaα form is generated. This form is subsequently reacted to the FXaβ form by autoproteolytic activity and cleavage of the C-terminus of the heavy chain between Arg469 and Gly470. For the preparation of factor X expression plasmids leading to the production of factor XΔ analogues, which will be present after activation exclusively in the Fxaα form having intact β-peptide, the amino acid Arg469 was mutated to Lys so that the C-terminal region of the heavy chain can not be processed any more.

For this purpose, the DNA sequence of factor X encoding the C-terminal amino acid sequence was removed from position 1363 to the stop signal by partial BstEII-SpeI digestion and replaced by two ligated oligonucleotide pairs. Oligonucleotide #0005 (5'-GTC ACC GCC TTC CTC AAG TGG ATC GAC AGG TCC ATG AAA ACC AAG GGC TTG CCC AAG-3') (SEQ ID NO:39) and oligonucleotide #0006 (5'-TTG GCC TTG GGC AAG CCC TTG GTT TTC ATG GAC CTG TCG ATC CAC TTG AGG AAG GCG-3') (SEQ ID NO:40) were ligated with oligonucleotide #0007 (5'-GCC AAG AGC CAT GCC CCG GAG GTC ATA ACG TCC TCT CCA TTA AAG TGA GAT CCC A-3') (SEQ ID NO:41) and oligonucleotide #0008 (5'-CTA GTG GGA TCT CAC TTT AAT GGA GAG GAC GTT ATG ACC TCC GGG GCA TGG CTC-3') (SEQ ID NO:42). The mutation of amino acid Arg469 is introduced by the oligonucleotide pair #0005–0006. FIG. 7 is a schematic representation of the FXΔ analogues.

EXAMPLE 7

Figure 8:
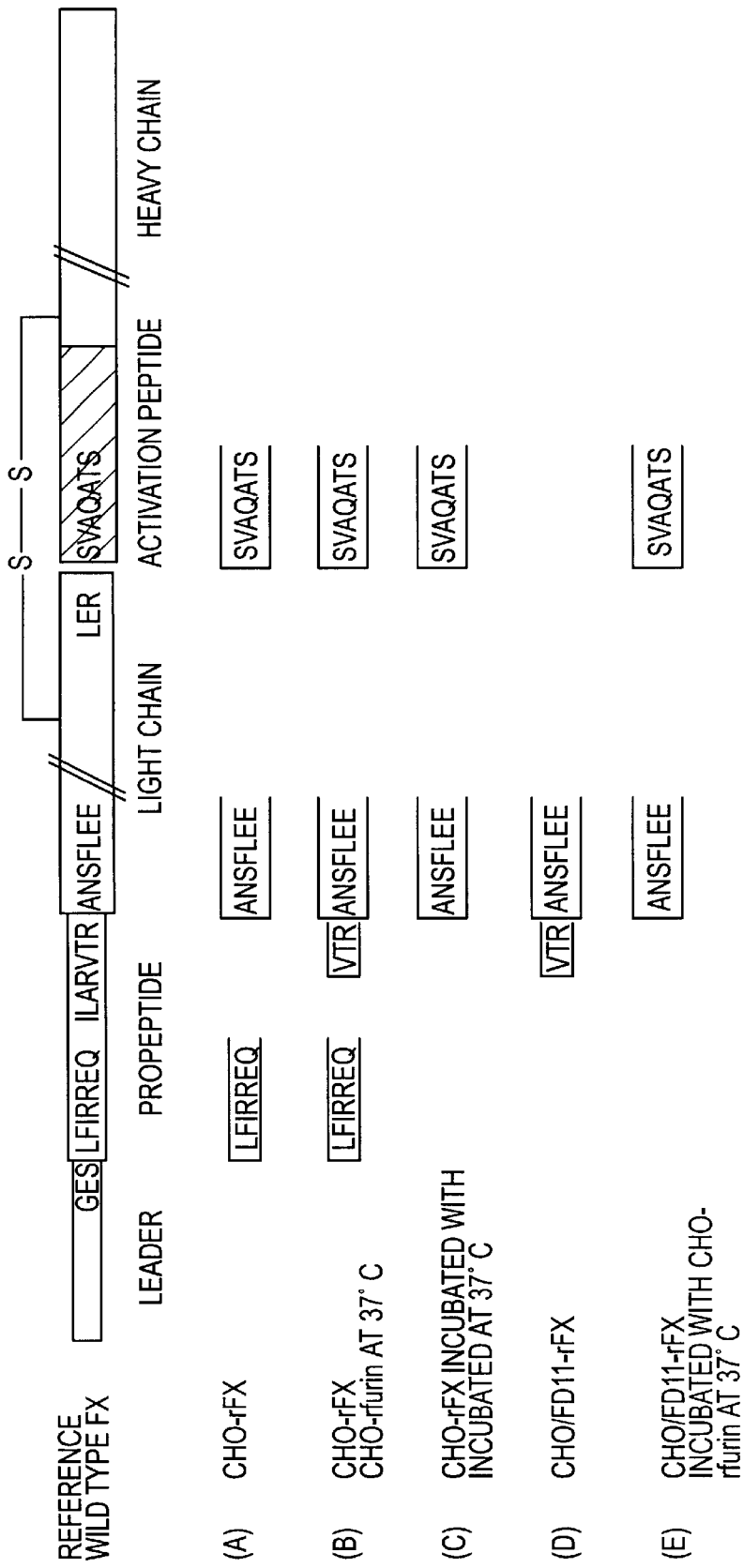
FIG. 8 shows a schematic representation of the N-termini of rfactor X processing products from CHO, CHO/r-furin and furin deficient cells (SEQ ID NOS:99–104).

Determination of the N-termini of Factor X and Processing Products With and Without r-Furin Recombinant factor X was expressed in CHO cells having endogenous furin, as described in Example 1, and in furin deficient cells, as described in Example 5. rFactor X was isolated from cell culture supernatant of highly expressing CHO-rFX clones, which was a) not pre-treated, b) incubated at 37° C. for 12 hours and c) pre-treated with CHO-r-furin supernatant at 37° C. for 12, hours, as well as from cell culture supernatant of CHO-FD11-rFX clones which was d) not pre-treated and e) pre-treated with CHO-r-furin supernatant at 37° C. for 12 hours. The terminal N-terminal amino acids of factor X and the processing products of the individual reaction mixtures a) to e) were determined by Edman analysis. FIG. 8 is a schematic representation of the results.

rFactor X from highly expressing CHO cells is present in the form of the mature heavy and light chains as well as in the single chain form, partly still containing propeptide. After incubation of these cell culture supernatants for 12 hours at 37° C. (b), additional faulty N-termini of the rFX light chain having 3 additional amino acids Val38-Thr39-Arg40 are formed, as described by Wolf et al. (1991, J. Bio. Chem. 266:13726–13730). These cryptic ends are also found when sequencing rFX material from non-pre-treated CHO-FD11 cells (d). This observation shows that the formation of these faulty N-termini can be prevented by reasonable conditions, i.e. cell culture conditions, storage and purifying processes in order to minimize rFX proteolysis by CHO proteases.

Contrary to the purified material from CHO cells (a and b), rFX from non-amplified, furin deficient cells (d) is only present in the form of unprocessed single chain precursors. N-terminal sequences corresponding to the propeptide portion are not found, either. This shows that single chain rFX precursor is not processed any more to light/heavy chain in furin deficient CHO cells (d), which suggests a central role of the endoprotease furin in this processing step in vivo. In addition, it shows that rFX molecules containing propeptide are also processed in furin deficient CHO cells, i.e. that furin does not play an essential role in this processing step in vivo. After incubation of rFX from CHO cells (c) and CHO-FD11 cells (e) in the presence of furin, only light and heavy chains having correct N-termini are found. This proves that the single chain FX precursors as well as the propeptide containing rFX molecules are reacted to homogenous, mature factor X by in vitro processing. Thus, factor X processed in the presence of furin exhibits exceptional structural integrity.

EXAMPLE 8

Expression and Characterization of the Recombinant FX Deletion Mutant Having the Furin Cleavage Site Arg-Val-Thr-Arg/Ile (SEQ ID NO:101) (FXΔ$^{RVTR/I}$)

Figure 9:
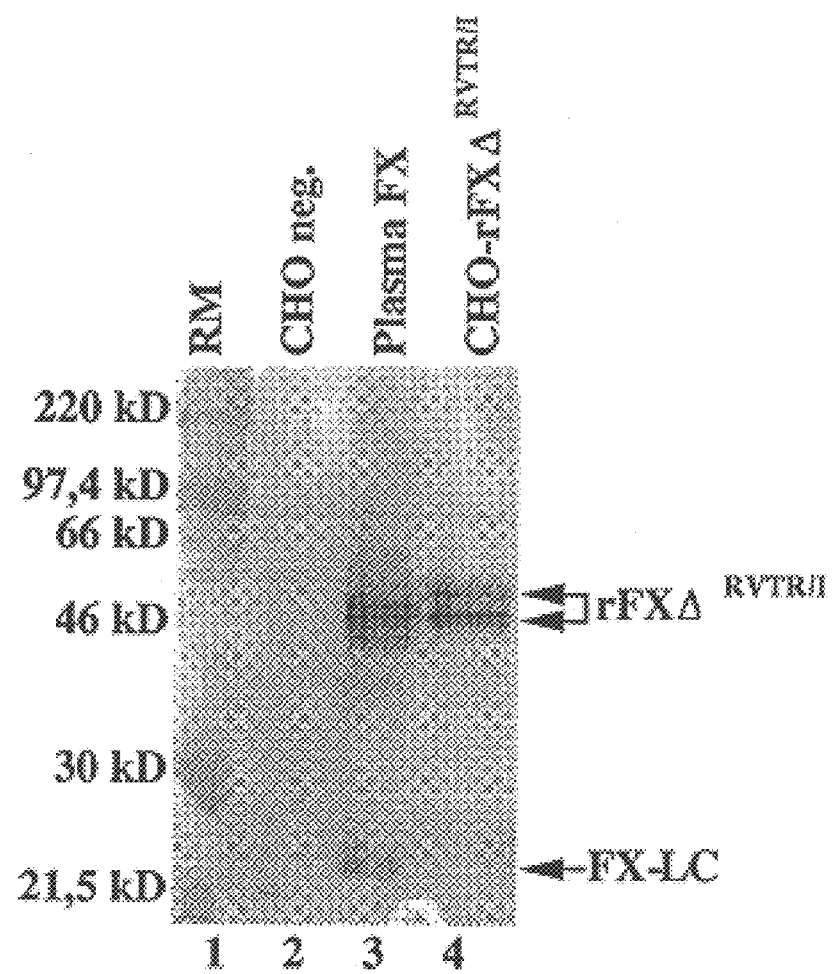
FIG. 9 shows a Western blot analysis of rfactor XΔ$^{RVTR/I}$ expressed in CHO cells.

The expression plasmid encoding the FX deletion mutant having the cleavage site Arg-Val-Thr-Arg/Ile (SEQ ID NO:101) (FXAΔ$^{RVTR/I}$) was co-transfected with the selection marker pSV/dhfr in dhfr deficient CHO cells as described in Example 1. The recombinant protein FXAΔ$^{RVTR/I}$ from permanent CHO clones was characterized by means of Western blot analysis. As can be seen in FIG. 9, lane 4, the recombinant protein is present in the form of a double band of approximately 56 and 50 kD. No FX reactive material is detectable in the cell culture supernant of non-transfected CHO cells (lane 2). According to these results, it is impossible that these protein bands result from impurities of the analyzed supernatants of wild type FX from the residues of bovine serum in the cell culture medium. Therefore, the double band is possibly caused by different post-translational modifications, e.g. the presence of the propeptide or different glycosylation of the rFXAΔ$^{RVTR/I}$ molecule.

The cleavage site Arg-Val-Thr-Arg/Ile (SEQ ID NO:101) inserted into this construct is identical with the propeptide cleavage site of the wild type FX molecule, which is efficiently recognized and cleaved in vivo by a CHO endoprotease (see Example 7). The Western blot analysis shows no additional 35 kD and 31 kD heavy FX molecules, which would correspond to the activated α- and β-forms of the rFXAΔ$^{RVTR/I}$ heavy chain. These results show that either the amount of endoprotease is not sufficient to activate the protein or/and that the cleavage site Arg-Val-Thr-Arg/Ile (SEQ ID NO:101) is not or not effectively recognized and cleaved in vivo in the present sequence environment. Consequently, rFXAΔ$^{RVT/I}$ is practically only present in the single chain form.

EXAMPLE 9

Activation of the Recombinant rFXAΔ$^{RVTR/I}$ Protein by Means of Recombinant Furin Derivatives In Vitro Although the cleavage site Arg-Val-Thr-Arg/Ile (SEQ ID NO:101) in the rFX propeptide is recognized in vivo by a protease other than furin, Example 2 proves that this sequence is cleaved very efficiently and correctly by an r-furin derivative in vitro.

Figure 10:
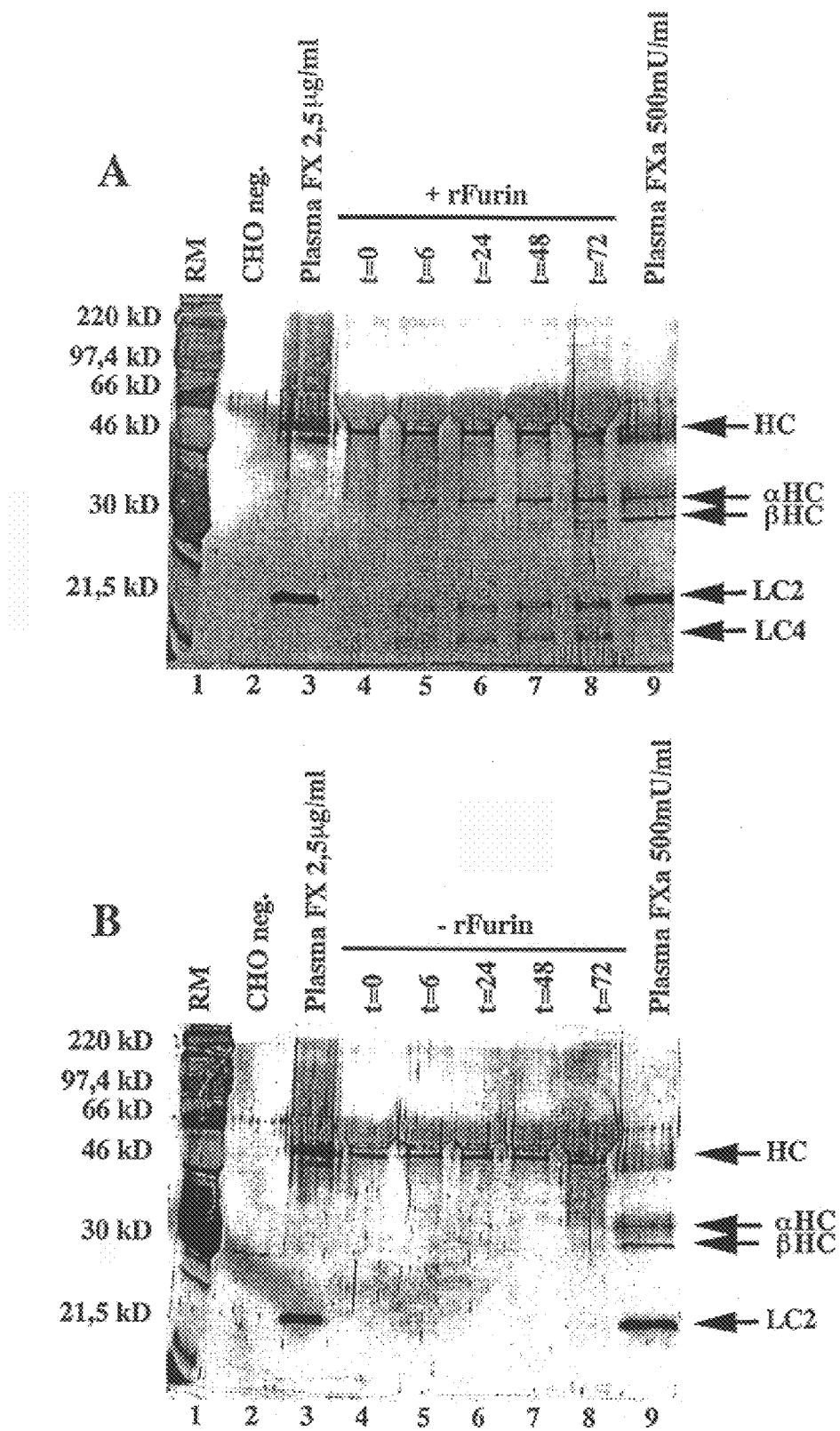
FIGS. 10A and 10B show a Western blot analysis of rfactor XΔ$^{RVTR/I}$ after in vitro activation with furin derivative.

Mixing experiments were carried out in order to test the ability of rFXAΔ$^{RVTR/I}$ protein to be activated by r-furin in vitro. Cell culture supernatant from CHO-FXAΔ$^{RVTR/I}$ cells were mixed with purified r-furin derivative r-furinΔCys-spacer-10xHis (see patent application EP-0 775 750-A2) in the presence of 20 mM Hepes pH 7.0, 150 mM NaCl, 4 mM CaCl$_2$ and 0.1% BSA at a ratio of 1:1. In control experiment, the CHO-rFXAΔ$^{RVTR/I}$ supernatant was mixed only with BSA containing buffer at the same ratio. The addition of BSA is meant to stabilize the enzymatic activity of the r-furin derivative and the activated rFXAΔ$^{RVTR/I}$ products consequently formed. Aliquots of the reaction mixture were tested before and after an incubation period of 6, 24, 48 and 72 hours (t=0, t=6, t=24, t=48, t=72) at 37° C. for rFXAΔ$^{RVTR/I}$ processing by means of Western blot analysis (FIGS. 10A and 10B). In the mixing experiment without r-furin addition (FIG. 10B), no change in the band pattern is visible during the incubation period (lanes 4 to 9). Due to the presence of BSA in the reaction mixtures, only the lighter rFXAΔ$^{RVTR/I}$ molecules (50 kD) are easily visible, because the 56 kD heavy molecules are covered by the BSA band. In the presence of the r-furin derivative (FIG. 10A), a 35 kD protein band appears already after 6 hours of incubation (lane 5), which corresponds to the α-form of the FX heavy chain (cf. lane 9). This protein accumulates in the course of incubation and is subsequently reacted to the proteolytic β-form, as already known in the case of plasma FX, which β-form forms by proteolytic conversion from the α-form (lanes 7 and 8). Light chains of 22 kD and 20 kD appear parallel to the detection of the activated forms of the heavy chains, which light chains were identified as propeptide free, carboxylated LC2 form (corresponding to the actually functional form) or as propeptide free, hypocarboxylated LC4 form of the light chain in Example 1.b. The presence of the hypocarboxylated LC4 form proves that the post-translational modification mechanisms are limited in the analyzed CHO clones. Although the 50 kD bond appears to be unchanged, while apparently the 56 kD form is directly degraded to light/heavy chains, in fact the 56 kD molecule at first is converted into the 50 kD form, and only subsequently is cleaved into a light and a heavy chain. This is due to the presence of the propeptide in the 56 kD molecule which at first is removed by forming the 50 kD form.

This proves that the rFXAΔ$^{RVTR/I}$ construct can be activated in vitro by r-furin derivatives via an inserted Arg-Val-Thr-Arg/Ile (SEQ ID NO:101) cleavage site and the resulting processing products of the rFXAΔ$^{RVTR/I}$ construct correspond to those of plasma FXa in size. The emergence of FXAβ, which is formed due to autoproteolytic processing of FXAα, shows the functionality of the rFXAΔ$^{RVTR/I}$ molecule.

What is claimed is:

1. A factor XΔ analogue comprising a factor X amino acid sequence in which amino acids Arg180 to Arg234 of SEQ ID NO:44 are deleted, and having a modification in said amino acid sequence between Gly173 and Arg179 of SEQ ID NO:44, said modification resulting in a processing site for a protease that does not naturally cleave between Gly173 and Arg179 of SEQ ID NO:44.

2. A factor XΔ analogue as set forth in claim 1, wherein said modification is at least one amino acid exchange in the region of said amino acid sequence between Gly173 and Arg179 of SEQ ID NO:44.

3. A factor XΔ analogue as set forth in claim 1, comprising a factor X sequence wherein amino acids Gly173 to Arg179 and residue 235 of SEQ ID NO:44 have the sequence Gly173-R6-R5-R4-R3-R2-Arg179/R1(235), wherein a) R1 is an amino acid selected from the group consisting of Val, Ser, Thr, Ile and Ala, b) R2 is an amino acid selected from the group consisting of Glu, Thr, Pro, Gly, Lys and Arg, c) R3 is an amino acid selected from the group consisting of Leu, Phe, Lys, Met, Gln, Glu, Ser, Val, Arg and Pro, d) R4 is an amino acid selected from the group consisting of Thr, Asp, Asn, Ile, Ser, Met, Pro, Arg and Lys, e) R5 is an amino acid selected from the group consisting of Asn, Lys, Ser, Glu, Gin, Ala, His and Arg, and f) R6 is an amino acid selected from the group consisting of Asp, Phe, Thr, Arg, Leu and Ser.

4. A factor XΔ analogue as set forth in claim 1, wherein the protease is selected from the group consisting of an endoprotease, a serine protease and a derivative of these proteases.

5. A factor XΔ analogue as set forth in claim 4, wherein said endoprotease is selected from the group consisting of kexin/Kex2, furin/PACE, PC1/PC3, PC2, PC4, PACE 4 and LPC/PC7 and said serine protease is selected from the group consisting of factor IIa, factor VIIa, factor IXa, factor XIIa, factor XIa, factor Xa and kallikrein.

6. A factor XΔ analogue as set forth in claim 1, wherein said factor XΔ analogue is present as a single chain polypeptide in enzymatically inactive form.

7. A factor XΔ analogue as set forth in claim 6, wherein said modification permits activation of the inactive, single-chain factor XΔ analogue polypeptide into the double-chain, active factor Xa analogue form.

8. A factor XΔ analogue as set forth in claim 1, further comprising a further modification at Lys370 and/or within a segment extending from Arg469 to Lys488 of SEQ ID NO:44.

9. A factor XΔ analogue as set forth in claim 8, wherein said further modification is located at a β-peptide cleavage site located between Arg469 and Gly470 of SEQ ID NO:44.

10. A factor XΔ analogue as set forth in claim 8, wherein said further modification is selected from the group consisting of a mutation, a deletion and an insertion, and is located between amino acid positions Arg469 and Ser476 of SEQ ID NO:44.

11. A factor XΔ analogue as set forth in claim 8, wherein said further modification prevents β-peptide from being cleaved off, the β-peptide extending from Gly470 to Lys488 of SEQ ID NO:44.

12. A factor XΔ analogue as set forth in claim 8, wherein said further modification is a deletion of the factor X β-peptide, which peptide extends from Gly470 to Lys488 of SEQ ID NO:44.

13. A factor XΔ analogue as set forth in claim 8, wherein the further modification is a translation stop signal.

14. A factor XΔ analogue as set forth in claim 13, wherein said translation stop signal is at the position of amino acid Gly470 of the factor X amino acid sequence.

15. A factor XΔ analogue as set forth in claim 6, wherein said modification in said amino acid sequence between Gly173 and Arg179 permits an in vitro activation of the inactive factor XΔ analogue to active factor XΔ analogue.

16. A factor XΔ analogue as set forth in claim 15, wherein said in vitro activation is effected by a protease selected from the group consisting of an endoprotease, a serine protease, and a derivative of these proteases.

17. A factor XΔ analogue as set forth in claim 16, wherein said endoprotease is selected from the group consisting of kexin/Kex2, furin/PACE, PC1/PC3, PC2, PC4, PACE 4, LPC/PC7, and said serine protease is selected from the group consisting of factor IIa, factor VIIa, factor IXa, factor XIIa, factor XIa, factor Xa and kallikrein.

18. A factor XΔ analogue as set forth in claim 1, comprising an intact β-peptide, wherein the β-peptide extends from Gly470 to Lys488 of SEQ ID NO:44, and the factor XΔ analogue is factor XΔα.

19. A preparation comprising purified factor XΔ analogue, said factor XΔ analogue having a factor X amino acid sequence in which amino acids Arg180 to Arg234 of SEQ ID NO:44 are deleted, and having a modification in said amino acid sequence between Gly173 and Arg179 of SEQ ID NO:44, said modification resulting in a processing site for a protease that does not naturally cleave between Gly173 and Arg179 of SEQ ID NO:44.

20. A preparation as set forth in claim 19, wherein said purified factor XΔ analogue is a single-chain factor XΔ analogue in enzymatically inactive form and having a purity of at least 80%, said purified factor XΔ analogue being free from inactive, proteolytic intermediates formed during processing or autoproteolysis of factor XΔ analogue or factor Xa analogue.

21. A preparation as set forth in claim 20, wherein said purity of said factor XΔ analogue is at least 90%.

22. A preparation as set forth in claim 20, wherein said purity of said factor XΔ analogue is at least 95%.

23. A preparation as set forth in claim 19, wherein the factor XΔ analogue is factor XΔα.

24. A preparation as set forth in claim 19, wherein the factor XΔ analogue is factor XΔβ.

25. A preparation as set forth in claim 19, wherein said factor XΔ analogue is a single-chain molecule in isolated form.

26. A preparation as set forth in claim 19, wherein the factor XΔ analogue of the preparation retains 100% of its original activity for at least a day.

27. A preparation as set forth in claim 25, wherein said modification permits in vitro activation of single-chain factor XΔ analogue to active factor Xa analogue.

28. A preparation as set forth in claim 19, said preparation being formulated as a pharmaceutical preparation.

29. A preparation as set forth in claim 28, said preparation being contained in a device in combination with a protease selected from the group consisting of an endoprotease, a serine protease and a derivative thereof.

30. A preparation as set forth in claim 29, wherein said endoprotease is selected from the group consisting of kexin/Kex2, furin/PACE, PC1/PC3, PC2, PC4, PACE 4, and LPC/PC7, and said serine protease is selected from the group consisting of factor IIa, factor VIIa, factor IXa, factor XIIa, factor XIa, factor Xa and kallikrein.

31. A preparation as set forth in claim 29, wherein said device is an application device adapted for administration of the preparation to a patient.

32. A preparation as set forth in claim 28, wherein said preparation and said protease are present separately in said device.

33. A preparation comprising a purified factor Xa analogue free from inactive intermediates formed during processing or autoproteolysis of factor XΔ analogue or factor Xa analogue, obtainable by activation of a factor XΔ analogue comprising a factor X amino acid sequence in which amino acids Arg180 to Arg234 of SEQ ID NO:44 are deleted, and having a modification in said amino acid sequence between Gly173 and Arg179 of SEQ ID NO:44, said modification resulting in a processing site for a protease that does not naturally cleave between Gly173 and Arg179 of SEQ ID NO:44.

34. A preparation as set forth in claim 33, wherein the active factor Xa analogue is a double-chain molecule in isolated form.

35. A preparation as set forth in claim 33, wherein said factor Xa analogue has a purity of at least 80%.

36. A preparation as set forth in claim 35, wherein purity of said factor Xa analogue is at least 90%.

37. A preparation as set forth in claim 35, wherein purity of said factor Xa analogue is at least 95%.

38. A preparation as set forth in claim 33, further comprising a physiologically acceptable carrier and being present in storage-stable form.

39. A preparation as set forth in claim 38, further comprising a component selected from the group consisting of a blood factor and an activated form of a blood factor.

40. A preparation as set forth in claim 39, wherein said component is at least one component having factor VIII bypass activity.

41. A preparation as set forth in claim 33, said preparation being formulated as a pharmaceutical composition.

42. A method for treating and preventing blood coagulation disorders in patients, comprising administering an effective dose of a preparation comprising purified factor XΔ analogue, said factor XΔ analogue comprising a factor X amino acid sequence in which amino acids Arg180 to Arg234 of SEQ ID NO:44 are deleted, and having a modification in said amino acid sequence between Gly173 and Arg179 of SEQ ID NO:44, said modification resulting in a processing site for a protease that does not naturally cleave between Gly173 and Arg179 of SEQ ID NO:44.

43. A method as set forth in claim 42, wherein said blood coagulation disorder is hemophilia.

44. A method as set forth in claim 42, wherein said blood coagulation disorder involves inhibitor antibody formation in hemophiliacs.

45. A method of preparing a preparation comprising purified recombinant factor XΔ analogue, said method comprising:
   a) providing a preparation comprising a recombinant factor XΔ analogue, wherein said factor XΔ analogue has a factor X amino acid sequence in which amino acid Arg180 to Arg234 of SEQ ID NO:44 are deleted, and having a modification in said amino acid sequence between Gly173 and Arg179 of SEQ ID NO:44, said modification resulting in a processing site for a protease that does not naturally cleave between Gly173 and Arg179 of SEQ ID NO:44;
   b) isolating said recombinant factor XΔ analogue as a single-chain polypeptide; and
   c) purifying said isolated, single-chain factor, recombinant XΔ analogue polypeptide.

46. A method as set forth in claim 45, wherein said providing step (a) comprises
   providing a nucleic acid encoding said factor XΔ analogue;
   transfecting a suitable cell; and
   expressing said factor XΔ analogue.

47. A method of preparing a preparation comprising factor Xa analogue, said method comprising:
   a) providing a preparation comprising a recombinant preparation of factor XΔ analogue, wherein said factor XΔ analogue has a factor X amino-acid sequence in which amino acid Arg180 to Arg234 of SEQ ID NO:44 are deleted, and having a modification in said amino acid sequence between Gly173 and Arg179 of SEQ ID NO:44, said modification resulting in a processing site for a protease that does not naturally cleave between Gly173 and Arg179 of SEQ ID NO:44;
   b) isolating said recombinant factor XΔ analogue as a single-chain polypeptide;
   c) purifying said isolated, single-chain, recombinant factor XΔ analogue polypeptide; and
   d) subjecting said purified single-chain, recombinant factor XΔ analogue polypeptide to an activation step to obtain said preparation containing activated factor Xa analogue.

48. A method as set forth in claim 47, wherein the activation step comprises contacting said single-chain, recombinant factor XΔ analogue polypeptide with a protease selected from the group consisting of an endoprotease, a serine protease and a derivative of these proteases, under conditions permitting cleavage of said single-chain, recombinant factor XΔ analogue polypeptide into the double-chain factor Xa analogue form.

49. A method as set forth in claim 48, wherein said endoprotease is selected from the group consisting of kexin/Kex2, furin/PACE, PC1/PC3, PC2, PC4, PACE 4 and LPC/PC7, and said serine protease is selected from the group consisting of factor IIa, factor VIIa, factor IXa, factor XIIa, factor XIa, factor Xa and kallikrein.

50. A method as set forth in claim 48, wherein said protease is immobilized.

51. A method as set forth in claim 47, wherein said factor Xa analogue is free from inactive intermediates formed during processing or autoproteolysis of factor XΔ analogue or factor Xa analogue.

52. A factor XΔ analogue as set forth in claim 8, wherein said further modification is located between amino acid positions Arg469 and Ser476, and/or at Lys370 of SEQ ID NO:44.

53. A factor XΔ analogue as set forth in claim 13, wherein said translation stop signal is at residues Lys370, Gly470, Ala474, or Ser476 of SEQ ID NO:44.

54. A factor XΔ analogue as set forth in claim 8, wherein said further modification is an amino acid substitution at one or more of the amino acid positions Arg469, Gly470, Lys370, Lys475 and Ser476 of said factor X amino acid sequence.

55. A preparation as set forth in claim 28, further comprising a component selected from the group consisting of a blood factor and an activated form of a blood factor.

56. A preparation as set forth in claim 55, wherein said component is at least one component having factor VIII bypass activity.

* * * * *